(12) United States Patent
Spindler et al.

(10) Patent No.: US 11,421,220 B2
(45) Date of Patent: Aug. 23, 2022

(54) ENGINEERED CELLS EXPRESSING ANTI-VIRAL T CELL RECEPTORS AND METHODS OF USE THEREOF

(71) Applicant: GigaMune, Inc., South San Francisco, CA (US)

(72) Inventors: Matthew James Spindler, San Francisco, CA (US); David Scott Johnson, San Francisco, CA (US); Ayla Lynn Nelson, San Francisco, CA (US); Ellen Kathleen Wagner, San Mateo, CA (US); Adam Shultz Adler, Belmont, CA (US); Yoong Wearn Lim, South San Francisco, CA (US); Michael Asensio, South San Francisco, CA (US)

(73) Assignee: GigaMune, Inc., San Francisco, CA (US)

( * ) Notice: Subject to any disclaimer, the term of this patent is extended or adjusted under 35 U.S.C. 154(b) by 0 days.

(21) Appl. No.: 17/480,697

(22) Filed: Sep. 21, 2021

(65) Prior Publication Data
US 2022/0002710 A1    Jan. 6, 2022

Related U.S. Application Data

(63) Continuation of application No. PCT/US2020/024028, filed on Mar. 20, 2020.

(60) Provisional application No. 62/821,808, filed on Mar. 21, 2019.

(51) Int. Cl.
*C40B 30/04* (2006.01)
*C12N 15/10* (2006.01)
*C07K 14/725* (2006.01)

(52) U.S. Cl.
CPC ...... *C12N 15/1058* (2013.01); *C07K 14/7051* (2013.01); *C12N 15/1037* (2013.01); *C40B 30/04* (2013.01)

(58) Field of Classification Search
None
See application file for complete search history.

(56) References Cited

U.S. PATENT DOCUMENTS

| 5,830,663 A | 11/1998 | Embleton et al. |
| 6,013,445 A | 1/2000 | Albrecht et al. |
| 6,858,412 B2 | 2/2005 | Willis et al. |
| (Continued) | | |

FOREIGN PATENT DOCUMENTS

| EP | 1516929 A2 | 3/2005 |
| JP | 2002-522067 A | 7/2002 |
| (Continued) | | |

OTHER PUBLICATIONS

Linnemann et al. (2013) Nature Medicine vol. 19 pp. 1534 to 1541.*
(Continued)

*Primary Examiner* — Christian C Boesen
(74) *Attorney, Agent, or Firm* — Fenwick & West LLP

(57) ABSTRACT

Provided herein are compositions comprising recombinant mammalian cells that express recombinant T cell rectors with specificity against EBV or CMV peptide:MHC antigens. Also provided are therapeutic methods of using the recombinant mammalian cells as cell therapies against viral infections.

14 Claims, 7 Drawing Sheets

Specification includes a Sequence Listing.

(56) References Cited

U.S. PATENT DOCUMENTS

| | | | |
|---|---|---|---|
| 7,749,697 | B2 | 7/2010 | Oleksiewicz et al. |
| 9,738,699 | B2 | 8/2017 | Johnson et al. |
| 2005/0041525 | A1 | 2/2005 | Pugia et al. |
| 2005/0064421 | A1 | 3/2005 | Gehrmann et al. |
| 2005/0221357 | A1 | 10/2005 | Shannon et al. |
| 2006/0108012 | A1 | 5/2006 | Barrow et al. |
| 2006/0134599 | A1 | 6/2006 | Toner et al. |
| 2006/0246477 | A1 | 11/2006 | Hermans et al. |
| 2007/0141048 | A1 | 6/2007 | Oleksiewicz et al. |
| 2009/0098555 | A1 | 4/2009 | Roth et al. |
| 2009/0105083 | A1 | 4/2009 | Hoogenboom et al. |
| 2010/0021896 | A1 | 1/2010 | Han |
| 2010/0151471 | A1 | 6/2010 | Faham et al. |
| 2010/0310558 | A1 | 12/2010 | Oleksiewicz et al. |
| 2010/0330571 | A1 | 12/2010 | Robbins et al. |
| 2011/0059556 | A1 | 3/2011 | Strey et al. |
| 2011/0201009 | A1 | 8/2011 | Quake et al. |
| 2013/0296535 | A1 | 11/2013 | Church et al. |
| 2014/0057799 | A1 | 2/2014 | Johnson et al. |
| 2014/0357500 | A1 | 12/2014 | Vigneault et al. |
| 2015/0004618 | A1 | 1/2015 | Warnatz et al. |
| 2015/0005199 | A1 | 1/2015 | Hindson et al. |
| 2015/0031555 | A1 | 1/2015 | Johnson et al. |
| 2015/0125865 | A1 | 5/2015 | Johnson et al. |
| 2015/0141261 | A1 | 5/2015 | Hunicke-Smith et al. |
| 2015/0154352 | A1 | 6/2015 | Johnson et al. |
| 2015/0167078 | A1 | 6/2015 | Johnson et al. |
| 2016/0152681 | A1 | 6/2016 | Hinrichs et al. |
| 2018/0258187 | A1 | 9/2018 | Cheung et al. |
| 2018/0258422 | A1* | 9/2018 | Johnson ............. C12N 15/1065 |

FOREIGN PATENT DOCUMENTS

| | | |
|---|---|---|
| JP | 2009-518053 A | 5/2009 |
| KR | 10-2007-0031923 A | 3/2007 |
| KR | 10-2012-0004939 A | 1/2012 |
| WO | WO 1993/003151 A1 | 2/1993 |
| WO | WO 2006/086406 A2 | 8/2006 |
| WO | WO 2008/104184 A2 | 9/2008 |
| WO | WO 2009/049889 A1 | 4/2009 |
| WO | WO 2010/126614 A2 | 11/2010 |
| WO | WO 2011/139371 A1 | 11/2011 |
| WO | WO 2012/083225 A2 | 6/2012 |
| WO | WO 2012/104851 A1 | 8/2012 |
| WO | WO 2013/096643 A1 | 6/2013 |
| WO | WO 2013/109935 A1 | 7/2013 |
| WO | WO 2013/112655 A1 | 8/2013 |
| WO | WO 2013/188772 A1 | 12/2013 |
| WO | WO 2013/192570 A1 | 12/2013 |
| WO | WO 2014/004124 A2 | 1/2014 |
| WO | WO 2014/011735 A1 | 1/2014 |
| WO | WO 2016/200577 A1 | 12/2016 |
| WO | WO 2018/075794 A1 | 4/2018 |
| WO | WO 2018/197492 A1 | 11/2018 |
| WO | WO 2019/036688 A1 | 2/2019 |
| WO | WO 2019/133853 A1 | 7/2019 |

OTHER PUBLICATIONS

"Interpretation of Hepatitis B Serologic Test Results," Department of Health & Human Services, Centers for Disease Control and Prevention, 2008, 1 page, Can be retrieved at <URL:https://www.cdc.gov/hepatitis/hbv/pdfs/serologicchartv8.pdf>.

Atanassov, Ivan I. et al., "A simple, flexible and efficient PCR-fusion/Gateway cloning procedure for gene fusion, site-directed mutagenesis, short sequence insertion and domain deletions and swaps," Plant Methods, 2009, vol. 5, No. 14, pp. 1-11.

Barbas et al., "Semisynthetic combinatorial antibody libraries: a chemical solution to the diversity problem," *Proceedings of the National Academy of Sciences*, PNAS, May 15, 1992, 89 (10), pp. 4457-4461.

Bonarius, H., et al., "Monitoring the T-Cell Receptor Repertoire at Single-Clone Resolution," PLOS ONE, Public Library of Science, US, vol. 11, No. 1, Dec. 20, 2006, pp. E55 1-10.

Boyd, S., et al., "Measurement and Clinical Monitoring of Human Lymphocyte Clonality by Massively Parallel V-D-J Pyrosequencing," Science Translational Medicine, Dec. 23, 2009, vol. 1, Issue 12 12ra23, pp. 1-8.

Brouzes, E., et al., "Droplet microfluidic technology for single-cell high-throughput screening," PNAS, Aug. 25, 2009, vol. 106, No. 34, pp. 14195-14200.

Chial, H., "Tumor Suppressor (TS) genes and the two-hit hypothesis," Nature Education 1 (1):177, 6 Pages, [online] 2008 [retrieved on Jun. 26, 2015] retrieved from the Internet <URL:http://www.nature.com/scitable/nated/topicpage/Tumor-Suppressor-TS-Genes-and-the-Two-887>.

Embleton, M.J., et al., "In-cell PCR from mRNA: amplifying and linking the rearranged immunoglobulin heavy and light chain V-genes within single cells," Nucleic Acids Research, 1992, vol. 20, No. 15, pp. 3831-3837.

Extended European Search Report for European Patent Application No. EP 11848932.7, dated Apr. 11, 2014, 10 Pages.

Freeman et al., "Profiling the T-cell receptor beta-chain repertoire by massively parallel sequencing," Genome Research, 2009, vol. 19, No. 10, pp. 1817-1824.

Gibson, D., et al., "Complete Chemical Synthesis, Assembly, and Cloning of a Mycoplasma genitalium Genome," Science, Feb. 29, 2008, vol. 319, pp. 1215-1220.

Hall et al., "Quantitative-Trait Loci on Chromosomes 1, 2, 3, 4, 8, 9, 11, 12, and 18 Control Variation in Levels of T and B Lymphocyte Subpopulations," The American Journal of Human Genetics, 2002, vol. 70, pp. 1172-1182.

Hardenbol, P., et al., "Highly Multiplexed molecular inversion probe genotyping: Over 10,000 targeted SNPs genotyped in a single tube assay," Genome Research, 2005, vol. 15, pp. 269-275.

Hardenbol, P., et al., "Multiplexed genotyping with sequence-tagged molecular inversion probes," Nature Biotechnology, Jun. 2003, vol. 21, No. 6, pp. 673-678.

Horton, R., et al., "Engineering hybrid genes without the use of restriction enzymes: gene splicing by overlap extension," Gene, 1989, vol. 77, No. 1, pp. 61-68.

Horton, R., et al., "Gene splicing by overlap extension: tailor-made genes using the polymerase chain reaction," Biotechniques, 1990, vol. 8, No. 5, pp. 528-535.

Hviid, T.V., "In-Cell PCR Method for Specific Genotyping of Genomic DNA from One Individual in a Mixture of Cells from Two Individuals: A Model Study with Specific Relevance to Prenatal Diagnosis Based on Fetal Cells in Maternal Blood," Clinical Chemistry, 2002, vol. 48, pp. 2115-2123.

International Search Report and Written Opinion, Patent Cooperation Treaty Application No. PCT/US2020/024028, dated Jun. 25, 2020, 10 pages.

International Search Report and Written Opinion, Patent Cooperation Treaty Application No. PCT/US2020/031018, dated Oct. 1, 2020, 9 pages.

Johnson, D., et al., "De novo discovery of a tissue-specific gene regulatory module in a chordate," Genome Research, 2005, vol. 15, pp. 1315-1324.

Johnson, L.A. et al., "Gene therapy with human and mouse T-cell receptors mediates cancer regression and targets normal tissues expressing cognate antigen," Blood, Jul. 16, 2009, vol. 14, No. 3, pp. 535-546; p. 535, second col. third paragraph; p. 536, first col. third paragraph; p. 537, first col. first paragraph, DOI: 10.1182/blood-2009-03-211714.

Johnston, K.P., et al., "Water-in-Carbon Dioxide Microemulsions: An Environment for Hydrophiles Including Proteins," Science, Feb. 2, 1996, vol. 271, pp. 624-626.

Jostock, T. et al. "Rapid generation of functional human IgG antibodies derived from Fab-on-phage display libraries," Journal Immunological Methods, vol. 289, No. 1-2, May 17, 2004, pp. 65-80.

Katz, B., et al., "Therapeutic targeting of CD19 in hematological malignancies: past, present, future and beyond," Leukemia & Lymphoma, May 2014, pp. 999-1006, Informa Healthcare.

(56) References Cited

OTHER PUBLICATIONS

Kiss, M.M., et al., "High-Throughput Quantitative Polymerase Chain Reaction in Picoliter Droplets," Anal. Chem., 2005, vol. 80, pp. 8975-8981.
Maheswaran, S., et al., "Detection of Mutations in EGFR in Circulating Lung-Cancer Cells," The New England Journal of Medicine, 2008, vol. 359, pp. 366-377.
Markoulatos, P., et al., "Multiplex Polymerase Chain Reaction: A Practical Approach," Journal of Clinical Laboratory Analysis, 2002, vol. 16, pp. 47-51.
Monod, M.Y., et al., "IMGT/JunctionAnalysis: the first tool for the analysis of the immunoglobulin and T cell receptor complex V-J and V-D-J Junctions," Bioinformatics, 2004, vol. 20, pp. 1379-1385.
Moskalev, E., et al., "Correction of PCR-bias in quantitative DNA methylation studies by means of cubic polynomial regression", Nucleic Acids Research, 2011, vol. 39, No. 11, 12 pages.
Nagrath, S., et al., "Isolation of rare circulating tumour cells in cancer patients by microchip technology," Nature, 2007, vol. 450, pp. 1235-1239.
PCT International Search Report and Written Opinion dated May 13, 2013 for PCT/US2013/022843, 9 Pages.
PCT International Search Report and Written Opinion for PCT/US2013/022210, dated May 14, 2013, 10 Pages.
PCT International Search Report and Written Opinion for PCT/US2013/045864, dated Mar. 14, 2014, 12 Pages.
PCT International Search Report and Written Opinion for PCT/US2013/045904, dated Sep. 5, 2013, 12 Pages.
International Search Report and Written Opinion, Patent Cooperation Treaty Application No. PCT/US2016/033109, dated Oct. 19, 2016, 23 Pages.
PCT International Search Report and Written Opinion, Application No. PCT/US2011/065600, dated Apr. 9, 2012, 12 pages.
PCT International Search Report and Written Opinion, Application No. PCT/US2012/070989, dated Dec. 14, 2013, 7 pages.
PCT International Search Report and Written Opinion, Application No. PCT/US2013/047142, dated Oct. 18, 2013, 9 Pages.
PCT International Search Report and Written Opinion, Application No. PCT/US2013/049872, dated Oct. 8, 2013, 17 Pages.
PCT Invitation to Pay Additional Fees, and Where Applicable, Protest Fee, PCT/US2016/033109, dated Aug. 23, 2016, 5 Pages.
Porcelli et al., "Analysis of T Cell Antigen Receptor (TCR) Expression by Human Peripheral Blood CD4-8-α/β Cells Demonstrates Preferential Use of Several Vβ genes and an invariant TCR α chain," The Journal of Experimental Medicine, Jul. 1, 1993, vol. 178, pp. 1-16.
Porreca, G., et al., "Multiplex amplification of large sets of human exons," Nature Methods, Nov. 2007, vol. 4, No. 11, pp. 931-936.
Ravn, U., et al., "By-passing in vitro screening—next generation sequencing technologies applied to antibody display and in silico candidate selection," *Nucleic Acids Research*, vol. 38, Issue 21, Nov. 1, 2010, pp. 1-11, e193.
Reddy, S., et al., "Monoclonal antibodies isolated without screening by analyzing the variable-gene repertoire of plasma cells," Nature Biotechnology, Sep. 2010, vol. 28, No. 9, pp. 965-959.
Renaut, L., et al., "Chapter 26, Affinity maturation of antibodies: optimized methods to generate high-quality ScFv libraries and isolate IgG candidates by high-throughput screening," *Antibody Engineering and Protocols*, Second Edition, Methods in Molecular Biology, vol. 907, Jan. 1, 2007, pp. 451-461.
Robins, H., et al., "Comprehensive assessment of T-cell receptor β-chain diversity in αβ T cells," Blood, 2009, vol. 114, pp. 4099-4107.
Robins, H., et al., "Overlap and Effective Size of the Human $CD8^+$ T Cell Receptor Repertoire," Science Translational Medicine, Sep. 1, 2010, vol. 2, Issue 47 47ra64, pp. 1-9.
Roche, A.M., et al., "Antibody blocks acquisition of bacterial colonization through agglutination," Mucosal Immunol. Jan. 2015, pp. 176-185, vol. 8, Issue 1. doi:10.1038/mi.2014.55.
Sandberg, Y., et al., "BIOMED-2 Multiplex Immunoglobulin/T-Cell Receptor Polymerase Chain Reaction Protocols Can Reliably Replace Southern Blot Analysis in routine Clonality Diagnostics," Journal of Molecular Diagnostics, Oct. 2005, vol. 7, No. 4, pp. 495-503.
Shigematsu, H., et al., "Clinical and Biological Features Associated with Epidermal Growth Factor Receptor Gene Mutations in Lung Cancers," Journal of the National Cancer Institute, 2005, vol. 97, pp. 339-346.
Spindler, M.J., et al., "Massively parallel interrogation and mining of natively paired human TCRαβ repertoires," Nat Biotechnol. May 2020; 38(5): 609-619. doi:10.1038/s41587-020-0438-y.
Van Dongen, J.J.M., et al., "Design and standardization of PCR primers and protocols for detection of clonal immunoglobulin and T-cell receptor gene recombinations in suspect lymphoproliferations: Report of the BIOMED-2 Concerted Action BMH4-CT98-3936," Leukemia, 2003, vol. 17, pp. 2257-2317.
Venturi, V., et al., "A Mechanism for TCR Sharing between T Cell Subsets and Individuals Revealed by Pyrosequencing," The Journal of Immunology, 2011, pp. 4285-4294, vol. 186.
Venturi, V., et al., "Methods for comparing the diversity of samples of the T cell receptor repertoire," Journal of Immunological Methods, 2007, vol. 321, No. 1, pp. 182-195. DOI: 10.1016/j.jim.2007.01.019.
Wagner, A., et al., "Surveys of Gene Families Using Polymerase Chain Reaction: PCR Selection and PCR Drift", Systematic Biology, Jun. 1994, vol. 43, No. 2, pp. 250-261.
Warren et al., "Exhaustive T-cell repertoire sequencing of human peripheral blood samples reveals signatures of antigen selection and a directly measured repertoire size of at least 1 million clonotypes," Genome Research, Feb. 24, 2011, vol. 21, pp. 790-797.
Wurch, T., et al., "A modified overlap extension PCR method to create chimeric genes in the absence of restriction enzymes", Biotechnology Techniques, Sep. 1998, vol. 12, No. 9, pp. 653-657.
Xiao et al., "A high-throughput platform for population reformatting and mammalian expression of phage display libraries to enable functional screening as full-length IgG," *mAbs*, vol. 9, Issue 6, Jul. 2017, pp. 996-1006.
Yang, L., et al., "Rapid production of gene replacement constructs and generation of a green fluorescent protein-tagged centromeric marker in Aspergillus nidulans", Eukaryotic Cell, 2004, vol. 3, No. 5, pp. 1359-1362.
Zagordi et al., "Error correction of next-generation sequencing data and reliable estimation of HIV quasispecies", Nucleic Acids Research, Jul. 29, 2010, vol. 38, No. 21, pp. 7400-7409.
Zeng, Y., et al., High-Performance Single Cell Genetic Analysis Using Microfluidic Emulsion Generator Arrays, Anal. Chem., 2010, vol. 82, pp. 3183-3190.

\* cited by examiner g Polynucleic acid target #1
h Polynucleic acid target #2
i Solid support, such as a bead
j Physical reaction container or emulsion droplet
k Plasmablast or plasma cell a Left primer for target #1
b Right primer for target #1
c Primer region complementary to d
d Primer region complementary to c
e Left primer for target #2
f Right primer for target #2
g Polynucleic acid target #1
h Polynucleic acid target #2
i Solid support, such as a bead
j Physical reaction container or emulsion droplet a Left primer for target #1
b Right primer for target #1
c Primer region complementary to d
d Primer region complementary to c
e Left primer for target #2
f Right primer for target #2
g Polynucleic acid target #1
h Polynucleic acid target #2
j Physical reaction container or emulsion droplet c Product region complementary to d
d Product region complementary to c
g Polynucleic acid target #1
h Polynucleic acid target #2
j Physical reaction container or emulsion droplet c Product region complementary to d
d Product region complementary to c
e Polymerase
g Polynucleic acid target #1
h Polynucleic acid target #2
i Fused product between polynucleic acid targets #1 and #2
j Physical reaction container or emulsion droplet

ENGINEERED CELLS EXPRESSING ANTI-VIRAL T CELL RECEPTORS AND METHODS OF USE THEREOF

1. CROSS REFERENCE TO RELATED APPLICATIONS

This application is a continuation of PCT/US2020/024028, filed Mar. 20, 2020, which claims the benefit of U.S. Provisional Application No. 62/821,808, filed Mar. 21, 2019, each of which is hereby incorporated in its entirety by reference.

2. SEQUENCE LISTING

The instant application contains a Sequence Listing with 84 sequences which has been submitted via EFS-Web and is hereby incorporated by reference in its entirety. Said ASCII copy, created on Mar. 19, 2020, is named GGM002WOsequencelisting.txt, and is 89,000 bytes in size.

3. FIELD

Provided herein are T cell receptors (TCRs) with binding specificity for Epstein-Barr Virus (EBV) or Cytomegalovirus (CMV) and compositions comprising such TCRs, including non-natural DNA vectors encoding TCRs, pharmaceutical compositions, and non-natural cell therapies.

4. BACKGROUND

Human cytomegalovirus (CMV), or human herpesvirus-5 (HHV-5) is the type species of the virus genus Cytomegalovirus, which in turn is a member of the viral family known as Herpesviridae or herpesviruses. It is also commonly called CMV. HCMV infection is typically unnoticed in healthy people, but can be life-threatening for the immunocompromised, such as HIV-infected persons, organ transplant recipients, or newborn infants. Congenital cytomegalovirus infection can lead to significant morbidity and even death. After infection, HCMV remains latent within the body throughout life and can be reactivated at any time. Eventually, it may cause mucoepidermoid carcinoma and possibly other malignancies such as prostate cancer.

Ganciclovir (Cytovene) treatment is used as CMV therapy for people with depressed immunity who have either sight-related or life-threatening illnesses. Valganciclovir (Valcyte) is also effective CMV therapy and is given orally: it is a pro-drug that gets converted into ganciclovir in the body, but is much better absorbed orally than the latter. The therapeutic effectiveness is frequently compromised by the emergence of drug-resistant virus isolates. Foscarnet or cidofovir are only given to people with CMV resistant to ganciclovir, because foscarnet has notable nephrotoxicity, resulting in increased or decreased Ca2+ or P, and decreased Mg2+. There remains an opportunity to develop more efficacious therapies for CMV infections.

The Epstein-Barr virus (EBV), formally called Human gammaherpesvirus 4, is one of eight known human herpesvirus types in the herpes family, and is one of the most common viruses in humans.

It is best known as the cause of infectious mononucleosis ("mono" or "glandular fever"). It is also associated with various non-malignant, premalignant, and malignant Epstein-Barr virus-associated lymphoproliferative diseases such as Burkitt lymphoma, hemophagocytic lymphohistiocytosis, and Hodgkin's lymphoma; non-lymphoid malignancies such as gastric cancer and nasopharyngeal carcinoma; and conditions associated with human immunodeficiency virus such as hairy leukoplakia and central nervous system lymphomas. The virus is also associated with the childhood disorders of Alice in Wonderland Syndrome and acute cerebellar ataxia and, based on some evidence, higher risks of developing certain autoimmune diseases, especially dermatomyositis, systemic lupus erythematosus, rheumatoid arthritis, Sjögren's syndrome, and multiple sclerosis. About 200,000 cancer cases per year are thought to be attributable to EBV.

Infection with EBV occurs by the oral transfer of saliva and genital secretions. Most people become infected with EBV and gain adaptive immunity. In the United States, about half of all five-year-old children and about 90% of adults have evidence of previous infection. Infants become susceptible to EBV as soon as maternal antibody protection disappears. Many children become infected with EBV, and these infections usually cause no symptoms or are indistinguishable from the other mild, brief illnesses of childhood. In the United States and other developed countries, many people are not infected with EBV in their childhood years. When infection with EBV occurs during adolescence, it causes infectious mononucleosis 35 to 50% of the time.

Currently, there are no drugs available for treatment or prevention of EBV infections. There remains a need and opportunity to develop anti-EBV therapeutics.

5. SUMMARY

Provided herein are novel TCRs with binding specificity for EBV or CMV.

Also provided are isolated polynucleotides encoding the TCRs provided herein, and portions thereof.

Also provided are vectors comprising such polynucleotides.

Also provided are recombinant host cells comprising such polynucleotides and recombinant host cells comprising such vectors.

Also provided are methods of producing the TCRs using the polynucleotides, vectors, or host cells provided herein.

Also provided are pharmaceutical compositions comprising the TCRs and a pharmaceutically acceptable excipient.

In some aspects, the present invention provides a pharmaceutical composition comprising the TCR and an excipient. In some embodiments, the TCR is in an amount sufficient as prophylaxis against infectious disease when administered to a subject. In some embodiments, the TCR is an amount sufficient to clear infectious disease in an individual actively fighting infection.

In other aspects, the present invention provides a method of treating a disease comprising the step of: administering an effective amount of the TCR or the pharmaceutical composition provided herein to a subject with the disease.

In some aspects, the present invention provides a mixture of polynucleotides encoding the TCRs provided herein. In other aspects, the present invention provides a mixture of vectors comprising the isolated polynucleotides. In other aspects, the present invention provides a mixture of host cell clones comprising the mixture of polynucleotides or vectors.

Some aspects of the present invention are related to a method of producing TCR, comprising: expressing the antibodies in host cells using a library of polynucleotide vectors, and isolating the cells that express the TCR.

TCRs of the invention may be transformed into T cells, rendering them capable of destroying cells presenting CMV or EBV peptide antigens, for administration to a patient in the treatment process known as adoptive therapy (see Zhao et al., (2007) J Immunol. 179: 5845-54; Robbins et al., (2008) J Immunol. 180:6 116-31; and WO2008/038002).

In other aspects, the present invention provides methods for discovery of TCRs from highly diverse mammalian T cell repertoires.

6. BRIEF DESCRIPTION OF THE DRAWINGS

FIG. 1 summarizes the method of discovering TCRs from transcripts expressed in peripheral blood TCRs isolated from virus seropositive human donors.

FIG. 2 summarizes a method of encapsulating T cells into physical containers with lysis mix and solid supports that capture nucleic acid targets from lysed cells.

FIG. 3 summarizes a method of encapsulating target-specific primers with nucleic acid targets affixed to solid supports.

Figure 1:
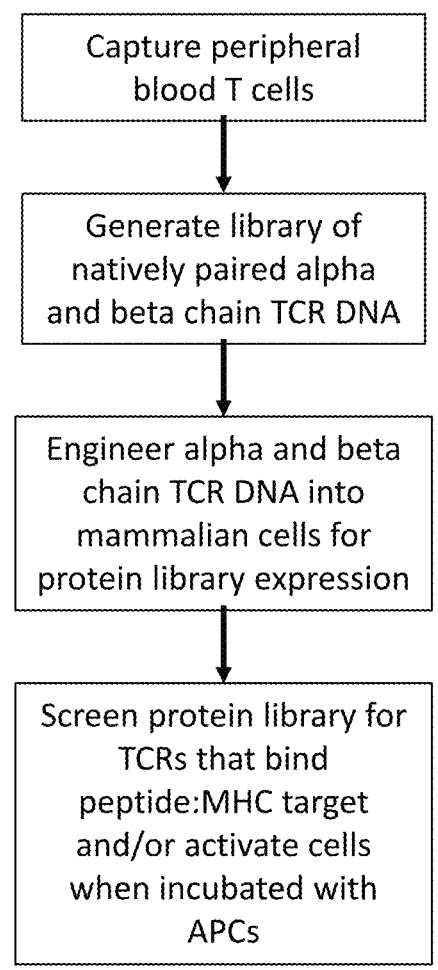
Figure 2:
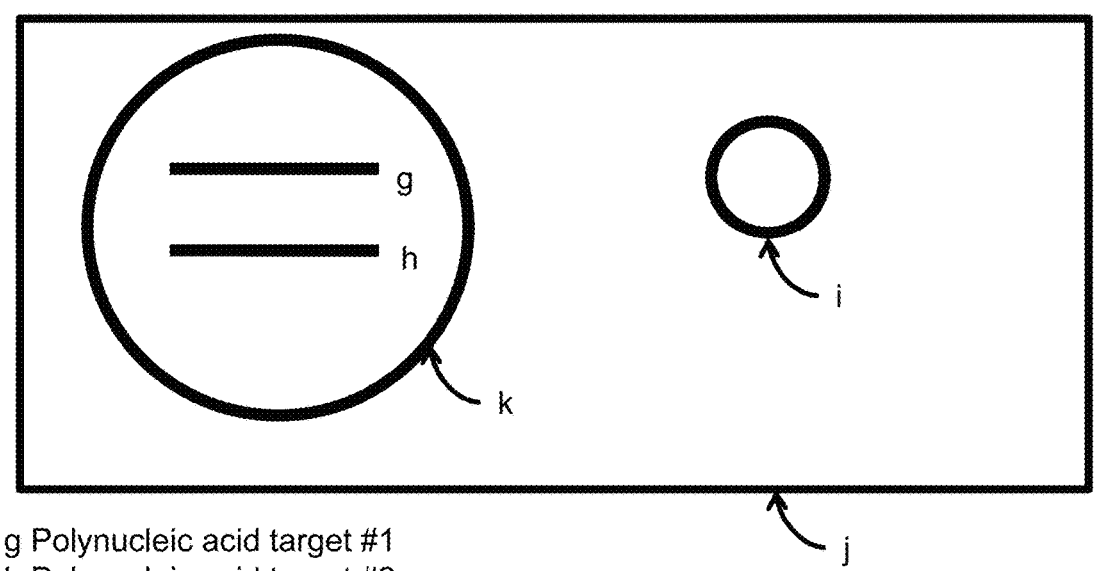
Figure 3:
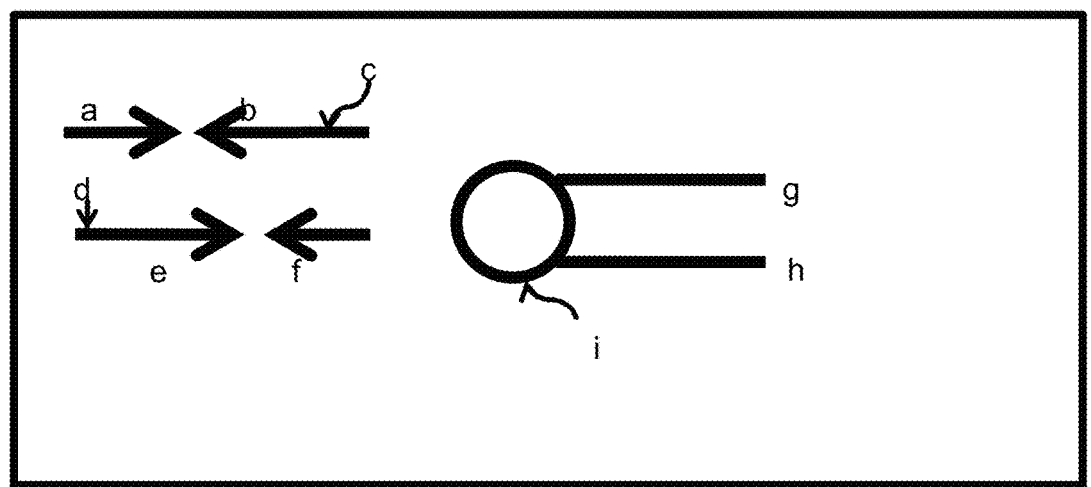
Figure 4:
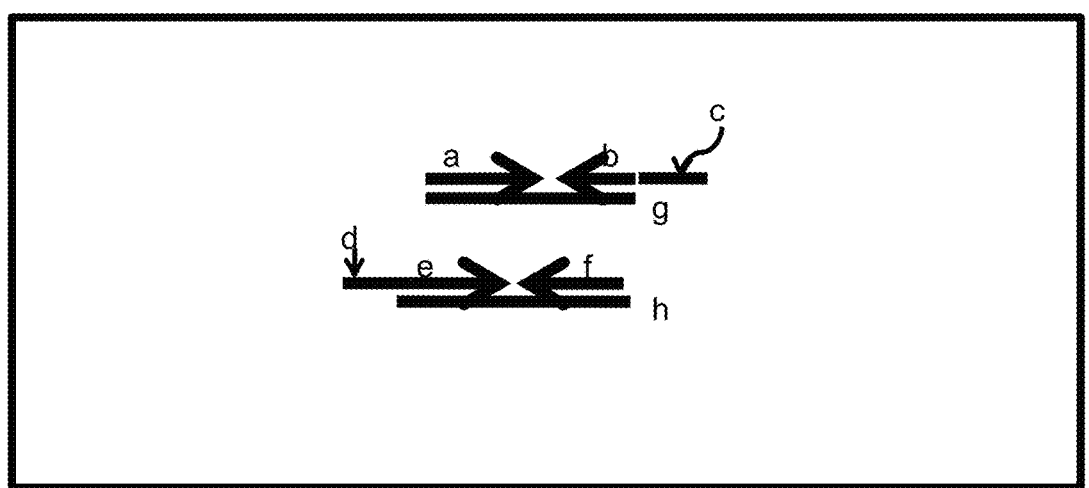
FIG. 4 shows the method of amplifying individual target nucleic acids with complementary regions.
Figure 5:
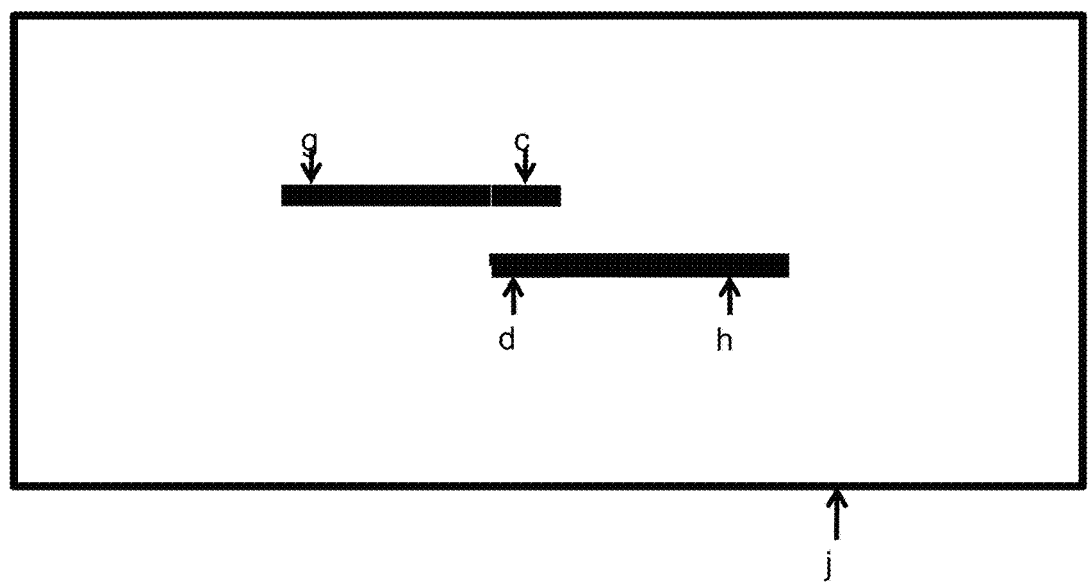
FIG. 5 shows the individual amplified target nucleic acids with complementary regions.
Figure 6:
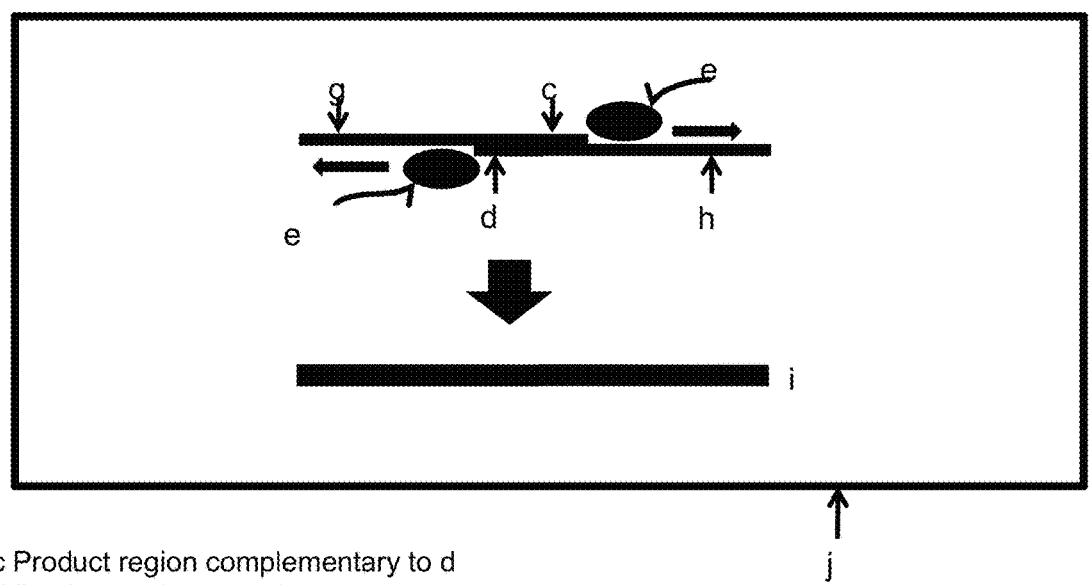

FIG. 6 summarizes a method of fusing separate amplified nucleic acid targets into single fused nucleic acid constructs.

Figure 7:
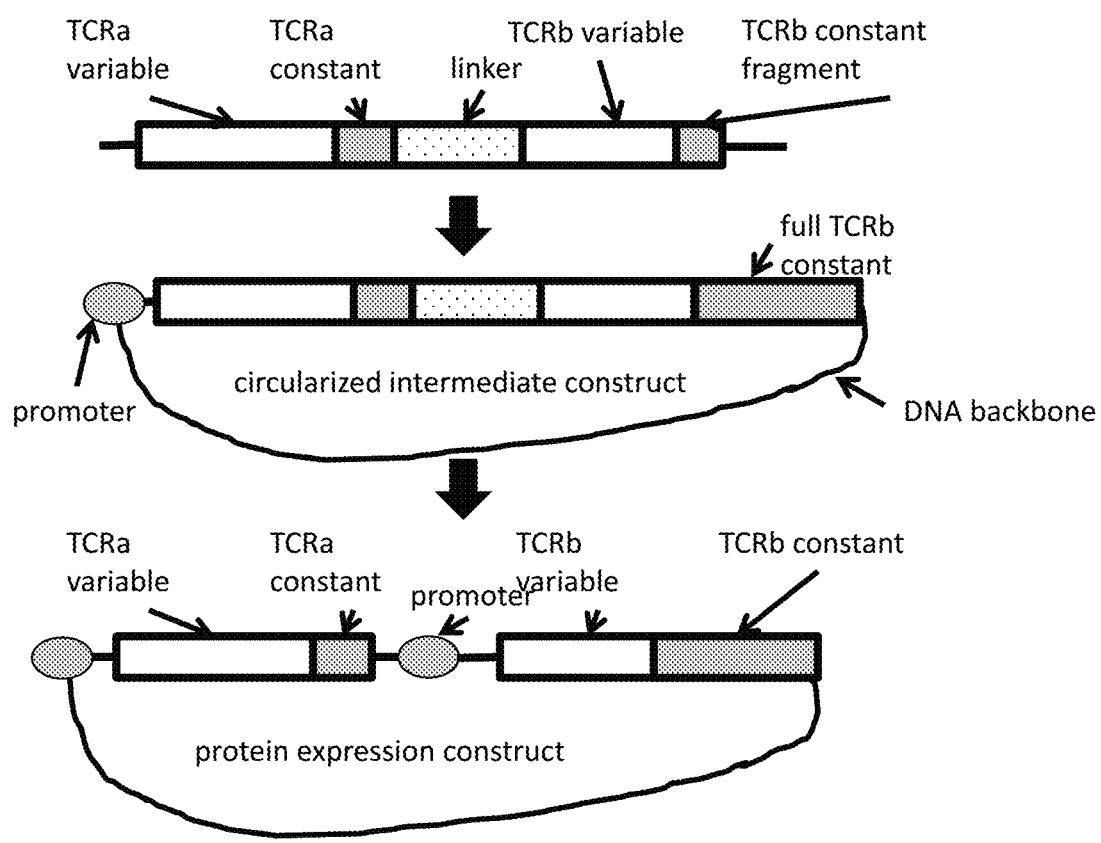

FIG. 7 shows the method of generating circularized gene expression constructs from the fused nucleic acid constructs.

7. DETAILED DESCRIPTION

7.1. Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Sambrook et al. *Molecular Cloning: A Laboratory Manual, 2d ed.*, Cold Spring Harbor Laboratory Press, Cold Spring Harbor, N.Y. (1989) and Ausubel et al., *Current Protocols in Molecular Biology*, Greene Publishing Associates (1992), and Harlow and Lane *Antibodies: A Laboratory Manual* Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well-known and commonly used in the art. Standard techniques can be used for chemical syntheses, chemical analyses, pharmaceutical preparation, formulation, and delivery, and treatment of patients.

The following terms, unless otherwise indicated, shall be understood to have the following meanings:

The term "T cell receptor", or "TCR", is a molecule found on the surface of T cells, or T lymphocytes, that is responsible for recognizing fragments of antigen as peptides bound to major histocompatibility complex (MHC) molecules. The TCR is composed of two different protein chains (that is, it is a heterodimer). In humans, in 95% of T cells the TCR consists of an alpha ($\alpha$) chain and a beta ($\beta$) chain (encoded by TRA and TRB, respectively), whereas in 5% of T cells the TCR consists of gamma and delta ($\gamma/\delta$) chains (encoded by TRG and TRD, respectively). This ratio changes during ontogeny and in diseased states (such as leukemia). It also differs between species. Each locus can produce a variety of polypeptides with constant and variable regions. When the TCR engages with antigenic peptide and MHC (peptide: MHC), the T lymphocyte is activated through signal transduction, that is, a series of biochemical events mediated by associated enzymes, co-receptors, specialized adaptor molecules, and activated or released transcription factors. The TCR is a disulfide-linked membrane-anchored heterodimeric protein normally consisting of the highly variable alpha ($\alpha$) and beta ($\beta$) chains expressed as part of a complex with the invariant CD3 chain molecules. T cells expressing this receptor are referred to as $\alpha$:$\beta$ (or $\alpha\beta$) T cells, though a minority of T cells express an alternate receptor, formed by variable gamma ($\gamma$) and delta ($\delta$) chains, referred as $\gamma\delta$ T cells. Each chain is composed of two extracellular domains: Variable (V) region and a Constant (C) region, both of Immunoglobulin superfamily (IgSF) domain forming antiparallel $\beta$-sheets. The Constant region is proximal to the cell membrane, followed by a transmembrane region and a short cytoplasmic tail, while the Variable region binds to the peptide/MHC complex. The variable domain of both the TCR $\alpha$-chain and $\beta$-chain each have three hypervariable or complementarity determining regions (CDRs). There is also an additional area of hypervariability on the $\beta$-chain (HV4) that does not normally contact antigen and, therefore, is not considered a CDR. The residues in these variable domains are located in two regions of the TCR, at the interface of the $\alpha$- and $\beta$-chains and in the $\beta$-chain framework region that is thought to be in proximity to the CD3 signal-transduction complex. CDR3 is the main CDR responsible for recognizing processed antigen, although CDR1 of the alpha chain has also been shown to interact with the N-terminal part of the antigenic peptide, whereas CDR1 of the $\beta$-chain interacts with the C-terminal part of the peptide. CDR2 is thought to recognize the MHC. CDR4 of the $\beta$-chain is not thought to participate in antigen recognition. The constant domain of the TCR consists of short connecting sequences in which a cysteine residue forms disulfide bonds, which form a link between the two chains. The generation of TCR diversity is similar to that for antibodies and B cell antigen receptors. It arises mainly from genetic recombination of the DNA encoded segments in individual somatic T cells by somatic V(D)J recombination using RAG1 and RAG2 recombinases. Unlike immunoglobulins, TCR genes do not undergo somatic hypermutation. Each recombined TCR possess unique antigen specificity, determined by the structure of the antigen-binding site formed by the $\alpha$ and $\beta$ chains in case of $\alpha\beta$ T cells or $\gamma$ and $\delta$ chains on case of $\gamma\delta$ T cells.

"Affinity" refers to the strength of the sum total of non-covalent interactions between a single binding site of a molecule (e.g., an RPP) and its binding partner (e.g., an antigen or epitope). Unless indicated otherwise, as used herein, "affinity" refers to intrinsic binding affinity, which reflects a 1:1 interaction between members of a binding pair (e.g., TCR and peptide:MHC). The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein. Affinity can be determined, for example, using surface plasmon resonance (SPR) technology (e.g., BIACORE®) or biolayer interferometry (e.g., FORTEBIO®).

"Avidity" refers to the accumulated strength of multiple affinities of individual non-covalent binding interactions, such as between a protein receptor and its ligand, and is commonly referred to as functional affinity. As such, avidity is distinct from affinity, which describes the strength of a single interaction. However, because individual binding events increase the likelihood of other interactions to occur (i.e. increase the local concentration of each binding partner in proximity to the binding site), avidity should not be thought of as the mere sum of its constituent affinities but as the combined effect of all affinities participating in the biomolecular interaction.

The "major histocompatibility complex" (MHC) is a set of cell surface proteins essential for the acquired immune system to recognize foreign molecules in vertebrates, which in turn determines histocompatibility. The main function of MHC molecules is to bind to antigens derived from pathogens and display them on the cell surface for recognition by the appropriate T-cells. The MHC determines compatibility of donors for organ transplant, as well as one's susceptibility to an autoimmune disease via crossreacting immunization. The human MHC is also called the HLA (human leukocyte antigen) complex (often just the HLA).

"MHC class I" molecules are one of two primary classes of MHC molecules and are found on the cell surface of all nucleated cells in the bodies of jawed vertebrates. They also occur on platelets, but not on red blood cells. Their function is to display peptide fragments of proteins from within the cell to cytotoxic T cells, often termed "peptide:MHC"; this will trigger an immediate response from the immune system against a particular non-self antigen displayed with the help of an MHC class I protein. Because MHC class I molecules present peptides derived from cytosolic proteins, the pathway of MHC class I presentation is often called cytosolic or endogenous pathway.

With regard to the binding of an TCR to a target peptide:MHC, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the RPP to the target molecule is competitively inhibited by the control molecule.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGALIGN (DNASTAR), CLUSTALW, CLUSTAL OMEGA, or MUSCLE software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution an amino acid with a chemically or functionally similar amino acid. Conservative substitution tables providing similar amino acids are well known in the art. By way of example, the groups of amino acids provided in TABLES 1-3 are, in some embodiments, considered conservative substitutions for one another.

TABLE 1

Selected groups of amino acids that are considered conservative substitutions for one another, in certain embodiments.

| | |
|---|---|
| Acidic Residues | D and E |
| Basic Residues | K R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

TABLE 2

Additional selected groups of amino acids that are considered conservative substitutions for one another, in certain embodiments.

| | |
|---|---|
| Group 1 | A, S, and T |
| Group 2 | D and E |
| Group 3 | N and Q |
| Group 4 | R and K |
| Group 5 | I, L, and M |
| Group 6 | F, Y, and W |

TABLE 3

Further selected groups of amino acids that are considered conservative substitutions for one another, in certain embodiments.

| | |
|---|---|
| Group A | A and G |
| Group B | D and E |
| Group C | N and Q |
| Group D | R, K, and H |
| Group E | I, L, M, V |
| Group F | F Y and W |
| Group G | S and T |
| Group H | C and M |

Additional conservative substitutions may be found, for example, in Creighton, *Proteins: Structures and Molecular Properties* 2nd ed. (1993) W. H. Freeman & Co., New York, N.Y. An RPP generated by making one or more conservative substitutions of amino acid residues in a parent RPP is referred to as a "conservatively modified variant."

The term "treating" (and variations thereof such as "treat" or "treatment") refers to clinical intervention in an attempt to alter the natural course of a disease or condition in a subject in need thereof. Treatment can be performed both for prophylaxis and during the course of clinical pathology. Desirable effects of treatment include preventing occurrence or recurrence of disease, alleviation of symptoms, diminish of any direct or indirect pathological consequences of the disease, preventing metastasis, decreasing the rate of disease progression, amelioration or palliation of the disease state, and remission or improved prognosis.

As used herein, the term "therapeutically effective amount" or "effective amount" refers to an amount of an RPP or pharmaceutical composition provided herein that, when administered to a subject, is effective to treat a disease or disorder.

As used herein, the term "subject" means a mammalian subject. Exemplary subjects include humans, monkeys, dogs, cats, mice, rats, cows, horses, camels, goats, rabbits, and sheep. In certain embodiments, the subject is a human. In some embodiments the subject has a disease or condition that can be treated with an RPP provided herein. In some aspects, the disease or condition is a cancer. In some aspects, the disease or condition is a viral infection.

The term "package insert" is used to refer to instructions customarily included in commercial packages of therapeutic or diagnostic products (e.g., kits) that contain information about the indications, usage, dosage, administration, combination therapy, contraindications and/or warnings concerning the use of such therapeutic or diagnostic products.

A "chemotherapeutic agent" refers to a chemical compound useful in the treatment of cancer. Chemotherapeutic agents include "anti-hormonal agents" or "endocrine therapeutics" which act to regulate, reduce, block, or inhibit the effects of hormones that can promote the growth of cancer.

The term "pharmaceutical composition" refers to a preparation which is in such form as to permit the biological activity of an active ingredient contained therein to be effective in treating a subject, and which contains no additional components which are unacceptably toxic to the subject.

The terms "modulate" and "modulation" refer to reducing or inhibiting or, alternatively, activating or increasing, a recited variable.

The terms "increase" and "activate" refer to an increase of 10%, 20%, 30%, 40%, 50%, 60%, 70%, 75%, 80%, 85%, 90%, 95%, 100%, 2-fold, 3-fold, 4-fold, 5-fold, 10-fold, 20-fold, 50-fold, 100-fold, or greater in a recited variable.

The terms "reduce" and "inhibit" refer to a decrease of 10%, 20%, 30%, 40%, 50%, 60%, 70%, 75%, 80%, 85%, 90%, 95%, 2-fold, 3-fold, 4-fold, 5-fold, 10-fold, 20-fold, 50-fold, 100-fold, or greater in a recited variable.

The term "effector T cell" includes T helper (i.e., CD4+) cells and cytotoxic (i.e., CD8+) T cells. CD4+ effector T cells contribute to the development of several immunologic processes, including maturation of B cells into plasma cells and memory B cells, and activation of cytotoxic T cells and macrophages. CD8+ effector T cells destroy virus-infected cells and tumor cells. See Seder and Ahmed, *Nature Immunol.*, 2003, 4:835-842, incorporated by reference in its entirety, for additional information on effector T cells.

The term "regulatory T cell" includes cells that regulate immunological tolerance, for example, by suppressing effector T cells. In some aspects, the regulatory T cell has a CD4+CD25+Foxp3+ phenotype. In some aspects, the regulatory T cell has a CD8+CD25+ phenotype. See Nocentini et al., *Br. J. Pharmacol.*, 2012, 165:2089-2099, incorporated by reference in its entirety, for additional information on regulatory T cells.

A "cytotoxic T cell" (also known as TC, cytotoxic T lymphocyte, CTL, T-killer cell, cytolytic T cell, CD8+ T-cell or killer T cell) is a T lymphocyte (a type of white blood cell) that kills cancer cells, cells that are infected (particularly with viruses), or cells that are damaged in other ways. Most cytotoxic T cells express T-cell receptors (TCRs) that can recognize a specific antigen. An antigen is a molecule capable of stimulating an immune response, and is often produced by cancer cells or viruses. Antigens inside a cell are bound to class I MHC molecules, and brought to the surface of the cell by the class I MHC molecule, where they can be recognized by the T cell. If the TCR is specific for that antigen, it binds to the complex of the class I MHC molecule and the antigen, and the T cell destroys the cell.

The term "in vivo" translates to "in the living", and refers to scientific studies in which the effects of various biological entities are tested on whole, living organisms or cells, usually animals, including humans, and plants, as opposed to a tissue extract or dead organism. This is not to be confused with experiments done in vitro ("within the glass"), i.e., in a laboratory environment using test tubes, Petri dishes, etc. Examples of investigations in vivo include: the pathogenesis of disease by comparing the effects of bacterial infection with the effects of purified bacterial toxins; the development of non-antibiotics, antiviral drugs, and new drugs generally; and new surgical procedures. Consequently, animal testing and clinical trials are major elements of in vivo research. In vivo testing is often employed over in vitro because it is better suited for observing the overall effects of an experiment on a living subject.

The term "recombinant" refers to proteins that result from the expression of recombinant DNA within living cells. Recombinant DNA is the general name for a piece of DNA that has been created by the combination of at least two separate segments of DNA.

The term "in vitro" translates to "in the glass", and refers to scientific studies that are performed with microorganisms, cells, or biological molecules outside their normal biological context. Colloquially called "test-tube experiments", these studies in biology and its subdisciplines are traditionally done in labware such as test tubes, flasks, Petri dishes, and microtiter plates. Studies conducted using components of an organism that have been isolated from their usual biological surroundings permit a more detailed or more convenient analysis than can be done with whole organisms; however, results obtained from in vitro experiments may not fully or accurately predict the effects on a whole organism. In contrast to in vitro experiments, in vivo studies are those conducted in animals, including humans, and whole plants.

A "variant" of a polypeptide (e.g., an antibody) comprises an amino acid sequence wherein one or more amino acid residues are inserted into, deleted from and/or substituted into the amino acid sequence relative to the native polypeptide sequence, and retains essentially the same biological activity as the native polypeptide. The biological activity of the polypeptide can be measured using standard techniques in the art (for example, if the variant is an antibody, its activity may be tested by binding assays, as described herein). Variants of the invention include fragments, analogs, recombinant polypeptides, synthetic polypeptides, and/or fusion proteins.

A "derivative" of a polypeptide is a polypeptide (e.g., an antibody) that has been chemically modified, e.g., via conjugation to another chemical moiety such as, for example, polyethylene glycol, albumin (e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06.

A "host cell" is a cell that can be used to express a nucleic acid, e.g., a nucleic acid of the invention Typically, a host cell is a cultured cell that can be transformed or transfected with a polypeptide-encoding nucleic acid, which can then be expressed in the host cell.

The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

"Cell therapy" (also called cellular therapy or cytotherapy) is therapy in which cellular material is injected, grafted or implanted into a patient; this generally means intact, living cells. For example, T cells capable of fighting cancer cells via cell-mediated immunity may be injected in the course of immunotherapy. A "TCR-T cell therapy" is a type of cellular therapy wherein at least one recombinant TCR sequence is engineered into autologous or allogeneic T cells, and then the engineered TCR-T cells are injected into a patient. In such applications, the TCR is directed against a peptide:MHC of therapeutic interest, for example, a virus peptide:MHC.

7.2. Other Interpretational Conventions

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless otherwise indicated, reference to a compound that has one or more stereocenters intends each stereoisomer, and all combinations of stereoisomers, thereof.

7.3. Nucleic Acids

In one aspect, the present invention provides isolated nucleic acid molecules. The nucleic acids comprise, for example, polynucleotides that encode all or part of a TCR, for example, one or both chains of a TCR of the invention, or a fragment, derivative, mutein, or variant thereof.

In another aspect, the present invention provides methods to generate libraries of nucleic acids that encode for libraries of TCRs, derived from primary T cells. These libraries of nucleic acids are generated by isolating T cells into single-cell reaction containers, wherein they are lysed and TCR-specific nucleic acids are purified or captured, for example on solid supports such as beads. The present invention provides methods for performing capture of transcripts from millions of single T cells in parallel. Capture of transcripts is followed by amplification of nucleic acids that encode TCR alpha and beta, and subsequent linkage of said nucleic acids into libraries of fused constructs that encode both TCR alpha and beta. In such libraries the native pairing of TCR alpha and beta, as originally found in the input T cells, is maintained. Such methods are performed in parallel on millions of single T cells, such that the resulting library of fused TCR alpha and beta nucleic acids comprises natively paired sequences for millions of single cells.

7.4. Expression Vectors

The present invention provides vectors comprising a nucleic acid encoding a polypeptide of the invention or a portion thereof. Examples of vectors include, but are not limited to, plasmids, viral vectors, non-episomal mammalian vectors and expression vectors, for example, recombinant expression vectors.

In another aspect of the present invention, expression vectors containing the nucleic acid molecules and polynucleotides of the present invention are also provided, and host cells transformed with such vectors, and methods of producing the polypeptides are also provided. The term "expression vector" refers to a plasmid, phage, virus or vector for expressing a polypeptide from a polynucleotide sequence. Vectors for the expression of the polypeptides contain at a minimum sequences required for vector propagation and for expression of the cloned insert. An expression vector comprises a transcriptional unit comprising an assembly of (1) a genetic element or elements having a regulatory role in gene expression, for example, promoters or enhancers, (2) a sequence that encodes polypeptides and proteins to be transcribed into mRNA and translated into protein, and (3) appropriate transcription initiation and termination sequences. These sequences may further include a selection marker. Vectors suitable for expression in host cells are readily available and the nucleic acid molecules are inserted into the vectors using standard recombinant DNA techniques. Such vectors can include promoters which function in specific tissues, and viral vectors for the expression of polypeptides in targeted human or animal cells.

The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, Trends Biochem. Sci. 11:287, Maniatis et al., 1987, Science 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The invention further provides methods of making polypeptides. A variety of other expression/host systems may be utilized. Vector DNA can be introduced into prokaryotic or eukaryotic systems via conventional transformation or transfection techniques. These systems include but are not limited to microorganisms such as bacteria (for example, $E.\ coli$) transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells useful in recombinant protein production include but are not limited to VERO cells, HeLa cells, Chinese hamster ovary (CHO) cell lines, or their derivatives such as Veggie CHO and related cell lines which grow in serum-free media (see Rasmussen et al., 1998, Cytotechnology 28:31) or CHO strain DX-B11, which is deficient in DHFR (see Urlaub et al., 1980, Proc. Natl. Acad. Sci. USA 77:4216-20) COS cells such as the COS-7 line of monkey kidney cells (ATCC CRL 1651) (see Gluzman et al., 1981, Cell 23:175), W138, BHK, HepG2, 3T3 (ATCC CCL 163), RIN, MDCK, A549, PC12, K562, L cells, C127 cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells, or any kind of primary cells, such as T cells Mammalian expression allows for the production of secreted or soluble polypeptides which may be recovered from the growth medium, or expression on the cell surface.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Once such cells are transformed with vectors that contain selectable markers as well as the desired expression cassette, the cells can be allowed to grow in an enriched media before they are switched to selective media, for example. The selectable marker is designed to allow growth and recovery of cells that successfully express the introduced sequences. Resistant clumps of stably transformed cells can be proliferated using tissue culture techniques appropriate to the cell line employed. An overview of expression of recombinant proteins is found in Methods of Enzymology, v. 185, Goeddell, D. V., ed., Academic Press (1990). Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods. The transformed cells can be cultured under conditions that promote expression of the polypeptide.

In addition, the polypeptides can be synthesized in solution or on a solid support in accordance with conventional techniques. Various automatic synthesizers are commercially available and can be used in accordance with known protocols. See, for example, Stewart and Young, Solid Phase Peptide Synthesis, 2d. Ed., Pierce Chemical Co. (1984); Tam et al., J Am Chem Soc, 105:6442, (1983); Merrifield, Science 232:341-347 (1986); Barany and Merrifield, The Peptides, Gross and Meienhofer, eds, Academic Press, New York, 1-284; Barany et al., Int J Pep Protein Res, 30:705-739 (1987).

The polypeptides and proteins of the present invention can be purified according to protein purification techniques well known to those of skill in the art. These techniques involve, at one level, the crude fractionation of the proteinaceous and non-proteinaceous fractions. Having separated the peptide polypeptides from other proteins, the peptide or polypeptide of interest can be further purified using chromatographic and electrophoretic techniques to achieve partial or complete purification (or purification to homogeneity). The term "purified polypeptide" as used herein, is intended to refer to a composition, isolatable from other components, wherein the polypeptide is purified to any degree relative to its naturally-obtainable state. A purified polypeptide therefore also refers to a polypeptide that is free from the environment in which it may naturally occur. Generally, "purified" will refer to a polypeptide composition that has been subjected to fractionation to remove various other components, and which composition substantially retains its expressed biological activity. Where the term "substantially purified" is used, this designation will refer to a peptide or polypeptide composition in which the polypeptide or peptide forms the major component of the composition, such as constituting about 50%, about 60%, about 70%, about 80%, about 85%, or about 90% or more of the proteins in the composition.

In some aspects, the present invention includes libraries of TCR-encoding nucleic acid vectors for integration into mammalian genomes. Such vectors include plasmids, retroviruses, and lentivirus. The libraries of nucleic acid vectors may include 10, 100, 1,000, 10,000, or more than 100,000 different antibody-encoding sequences. The sequences are derived from T cells. These libraries of nucleic acids are generated by isolating T cells into single-cell reaction containers, wherein they are lysed and antibody-specific nucleic acids are purified or captured, for example on solid supports such as beads. The present invention provides methods for performing capture of transcripts from millions of single T cells in parallel. Capture of transcripts is followed by amplification of nucleic acids that encode TCR alpha and beta, and subsequent linkage of said nucleic acids into libraries of fused constructs that encode both TCR alpha and beta. In such libraries the native pairing of TCR alpha and beta, as originally found in the input T cells, is maintained. Such methods are performed in parallel on millions of single T cells, such that the resulting library of fused TCR alpha and beta nucleic acids comprises natively paired sequences for millions of single cells. These paired fused amplicons are then engineered into full-length TCR constructs using Gibson Assembly, restriction endonucleases, or other recombinant DNA techniques.

Engineering into full-length TCR constructs is performed on the full library en masse, such that the TCR sequence content and TCR sequence counts of the library are essentially maintained throughout the process. In some aspects, the library of expression vectors is engineered in two steps, such that the TCR fragment amplicon is subcloned into an intermediate vector, and then a second round of Gibson Assembly, restriction digestion, or other recombinant technique is used to engineer additional domains of the antibody into the linker of the TCR fragment amplicon. The native pairing of TCR alpha and beta is essentially maintained throughout the process of engineering into full-length expression vector libraries. The vectors are designed in various orientations, for example, two separate promoters drive expression of TCR alpha and beta, or one promoter drives expression of both TCR alpha and beta, and a translational skip motif is used to separately translate the TCR alpha and beta into separate polypeptides. In some embodiments, the expression vectors comprise sequences for site-directed integration into mammalian production cells, for example, CRISPR-Cas9, Flp-In, Cre/Lox, or zinc finger recombination methods. Site-directed integration ensures that each mammalian production cell encodes a single TCR alpha and beta sequence, and decreases variability in expression levels between single production cells.

7.5. T Cell Receptors

Native TCRs exist in heterodimeric αβ or γδ forms. However, recombinant TCRs consisting of αα or ββ homodimers have previously been shown to bind to peptide MHC molecules. Therefore, the TCR of the invention may be a heterodimeric β TCR or may be an αα or ββ homodimeric TCR. For use in adoptive cell therapy, an b β heterodimeric TCR may, for example, be transfected as full-length chains having both cytoplasmic and transmembrane domains. In certain embodiments TCRs of the invention may have an introduced disulfide bond between residues of the respective constant domains, as described, for example, in WO 2006/000830. TCRs of the invention, particularly αβ heterodimeric TCRs, may comprise an α chain TRAC constant domain sequence and/or a β chain TRBC1 or TRBC2 constant domain sequence. The alpha and beta chain constant domain sequences may be modified by truncation or substitution to delete the native disulfide bond between Cys4 of exon 2 of TRAC and Cys2 of exon 2 of TRBC1 or TRBC2. The alpha and/or beta chain constant domain sequence(s) may also be modified by substitution of cysteine residues for Thr 48 of TRAC and Ser 57 of TRBC1 or TRBC2, the said cysteines forming a disulfide bond between the alpha and beta constant domains of the TCR. TCRs of the invention may be in single chain format, for example see WO 2004/033685. In certain embodiments single chain TCRs of the invention may have an introduced disulfide bond between residues of the respective constant domains, as described in WO 2004/033685.

The invention also provides a cell harbouring a vector of the invention, preferably a TCR expression vector. The vector may comprise nucleic acid of the invention encoding in a single open reading frame, or two distinct open reading frames, the alpha chain and the beta chain respectively. Another aspect provides a cell harbouring a first expression vector which comprises nucleic acid encoding the alpha chain of a TCR of the invention, and a second expression vector which comprises nucleic acid encoding the beta chain of a TCR of the invention. Such cells are particularly useful in adoptive TCR-T or other cell therapy. The cells may be isolated and/or recombinant and/or nonnaturally occurring and/or engineered.

Since the TCRs of the invention have utility in adoptive TCR-T therapy, the invention includes a nonnaturally occurring and/or purified and/or or engineered cell, especially a T cell, presenting a TCR of the invention. There are a number of methods suitable for the transfection of T cells with nucleic acid (such as DNA, cDNA or RNA) encoding the TCRs of the invention (see for example Robbins et al., (2008) J Immunol. 180: 6116-6131). T cells expressing the TCRs of the invention will be suitable for use in adoptive therapy-based treatment of cancers such as those of the pancreas and liver. As will be known to those skilled in the art, there are a number of suitable methods by which adoptive therapy can be carried out (see for example Rosenberg et al., (2008) Nat Rev Cancer 8(4): 299-308). TCR-T cells can be either derived from T cells in a patient's own blood (autologous) or derived from the T cells of another healthy donor (allogenic).

As is well-known in the art TCRs of the invention may be subject to post-translational modifications when expressed by transfected cells. Glycosylation is one such modification, which comprises the covalent attachment of oligosaccharide moieties to defined amino acids in the TCR chain. For example, asparagine residues, or serine/threonine residues are well-known locations for oligosaccharide attachment. The glycosylation status of a particular protein depends on a number of factors, including protein sequence, protein conformation and the availability of certain enzymes. Furthermore, glycosylation status (i.e oligosaccharide type, covalent linkage and total number of attachments) can influence protein function. Therefore, when producing recombinant proteins, controlling glycosylation is often desirable. Glycosylation of transfected TCRs may be controlled by mutations of the transfected gene (Kuball J et al. (2009), J Exp Med 206(2):463-475). Such mutations are also encompassed in this invention.

Certain TCRs of the invention may be in soluble form (i.e. having no transmembrane or cytoplasmic domains). For stability, TCRs of the invention, and preferably soluble β heterodimeric TCRs, may have an introduced disulfide bond between residues of the respective constant domains, as described, for example, in WO 03/020763. Some soluble TCRs of the invention are useful for making fusion proteins which can be used for delivering detectable labels or therapeutic agents to antigen presenting cells and tissues containing antigen presenting cells. They may therefore be associated (covalently or otherwise) with a detectable label (for diagnostic purposes wherein the TCR is used to detect the presence of cells presenting peptide:MHC; a therapeutic agent; or a pharmacokinetics-modifying moiety (for example by PEGylation). Detectable labels for diagnostic purposes include for instance, fluorescent labels, radiolabels, enzymes, nucleic acid probes and contrast reagents.

TCRs can be purified from host cells that have been transfected by a gene encoding the TCRs by elution of filtered supernatant of host cell culture fluid using a Heparin HP column, using a salt gradient, or other methods. Fragments or analogs of TCRs can be readily prepared by those of ordinary skill in the art following the teachings of this specification and using techniques well-known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known.

In certain embodiments, a TCR comprises one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative binding agent comprises one or more of monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymer is randomly attached to one or more side chains. In certain embodiments, PEG can act to improve the therapeutic capacity for a binding agent, such as a TCR. Certain such methods are discussed, for example, in U.S. Pat. No. 6,133,426, which is hereby incorporated by reference for any purpose.

7.6. Methods of Identifying T Cell Receptors

The variable region of TCRα and δ chains is encoded by a number of variable (V) and joining (J) genes, while TCRβ and γ chains are additionally encoded by diversity (D) genes. During VDJ recombination, one random allele of each gene segment is recombined with the others to form a functional variable region. Recombination of the variable region with a constant gene segment results in a functional TCR chain transcript. Additionally, random nucleotides are added and/or deleted at the junction sites between the gene segments. This process leads to strong combinatorial (depending on which gene regions will recombine) and junctional diversity (which and how many nucleotides will be added/deleted), resulting in a large and highly variable TCR repertoire, which will ensure the identification of a plethora of antigens. Additional diversity is achieved by the pairing of α and β or γ and δ chains to form a functional TCR.

VDJ recombination of the different TCR genes could theoretically generate between $10^{15}$ and $10^{20}$ TCR chains. The actual diversity present in a human body is estimated at around $10^{13}$ different clonotypes, implying that the aforedescribed seemingly random TCR development is obviously not random at all and is subject to different constraints. Moreover, while there are TCRs that are common in the general population, recent high-resolution studies have shown that the majority of TCRs is rare (in analogy to common vs. rare genomic variants). This is one of the reasons why precise methods are necessary to properly investigate complete individual immune repertoires.

Antibody discovery faces many of the same challenges as TCR discovery, but antibody discovery is far more technologically advanced than TCR discovery. For example, methods such as mouse hybridomas (Köhler & Milstein, *Nature*, 1975, 256(5517):495-7) and phage display (McCafferty et al., *Nature*, 1990, 348(6301):552-4) are widely used to quickly identify specific and efficacious antibody candidates. Though pioneering groups have described methods for yeast display of TCRs (Kieke et al., *PNAS*, 1999, 96(10):5651-6), such methods require artificial mutation of natural TCRs, which confounds broader utility. Additionally, TCRs are best studied in the context of T cell surface co-receptors, such as CD8 and CD3 (Kuhns et al., *Immunity*, 2006, 24(2):133-9). Thus, other groups have reported recombinant expression of TCR libraries in mammalian cells (Chervin et al., *Journal of Immunological Methods*, 2008, 339(2):175-84; Malecek et al., *Journal Immunological Methods*, 2013, 392(1-2):1-11). However, reported technologies fail to leverage the TCR diversity of natural human repertoires.

Recently, several groups have described methods that combine microfluidics, multiplex PCR, yeast display, and deep sequencing for ultra-high-throughput discovery of antibodies from human repertoires (Adler et al., *MAbs*, 2017, 9(8):1282-1296; Wang et al., *Nature Biotechnol*, 2018, 36(2):152-155). Here, we report a similar technology for ultra-high-throughput discovery of TCRs from human repertoires. Human repertoires can be virus-positive, healthy donors, cancer donors, donors with autoimmunity, or donors with any disease condition. Because the diversity of TCRαβ repertoires are generated by millions of single cells expressing different TCRα and TCRβ sequences, we first use a droplet microfluidic technology to isolate single cells into droplet emulsions and natively pair TCRα and TCRβ on a single cell level. The microfluidic technology can process millions of single T cells in an hour, which is significantly higher throughput than previously reported methods for TCRαβ pairing (Turchaninova et al., *Eur Journal of Immunology* 2013, 43(9):2507-15; Howie et al., *Science Translational Medicine* 2015, 7(301):301ra131). TCRα and TCRβ transcripts are captured from lysed single cells, amplified, and then physically linked into a single amplicon for subsequent cloning into expression vectors. Lysis and amplification are performed in two steps, since the reagents for lysis are incompatible with efficient RT-PCR.

Some other methods are available for natively pairing TCRα and TCRβ via a single cell barcoding method, for example through a commercial group (10× Genomics; Azizi et al., *Cell* 2018, 174(5):1293-1308.e36). Single cells are isolated into microfluidic droplets with molecular barcodes, and then TCRα and TCRβ from the single cells are fused to the unique barcodes. The single cell TCRα and TCRβ pairing is then inferred through bioinformatics. Though these molecular identifiers might offer advantages in terms of quantification, as used elsewhere for methods that do not leverage single cells (Shugay et al., 2014), single cell barcoding methods do not generate libraries of physically linked TCRα and TCRβ. This complicates any downstream efforts to identify binding and avidity properties of the TCRαβ sequences.

In our method, the library of millions of physically linked, natively paired TCRαβ amplicons is cloned en masse into expression vectors. The vectors are then subjected to restriction digestion en masse, and a DNA insert that encodes a TCR constant domain and translational skip sequence is cloned into the library. The full-length TCRαβ libraries are then packaged into lentiviral constructs and transduced into Jurkat cells that lack endogenous TCRβ expression and which are additionally engineered to stably express CD8. The resulting TCR-Jurkat libraries comprise natively linked TCRαβ sequences from millions of single T cells. The TCR-Jurkat libraries are immortal and renewable, enabling multiple rounds of panning with multiple antigens, using both binding to MHC multimers and activation by artificial antigen-presenting cells (aAPCs).

Similar methods can be applied to T cell repertoires from any animal with T cells, for example, mouse, rat, dog, cow, rabbit, or horse.

7.7. Sequences

Sequences 1-84, found in the sequence listing submitted with this application, comprise TCR α and β V(D)J polypeptides for the 42 TCRs described in Table 4. For example, TCR 1 comprises SEQ ID NO:1 (TCRα for TCR 1) and SEQ ID NO:2 (TCRβ for TCR 1), TCR 2 comprises SEQ ID NO:3 (TCRα for TCR 2) and SEQ ID NO:4 (TCRβ for TCR 2), TCR 3 comprises SEQ ID NO:5 (TCRα for TCR 3) and SEQ ID NO:6 (TCRβ for TCR 3), and so on.

7.8. Pharmaceutical Compositions

For administration to patients, the TCRs or TCR-T cells of the invention may be provided in a pharmaceutical composition together with one or more pharmaceutically acceptable carriers or excipients. TCR-T cells in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms. The pharmaceutical composition may be adapted for administration by any appropriate route, preferably a parenteral (including subcutaneous, intramuscular, or preferably intravenous) route. Such compositions may be prepared by any method known in the art of pharmacy, for example by mixing the active ingredient with the carriers) or excipient(s) under sterile conditions. TCRs, pharmaceutical compositions, vectors, nucleic acids and cells of the invention may be provided in substantially pure form, for example at least 50%, at least 60%, at least 70%, at least 80%, at least 85%, at least 90%, at least 91%, at least 92%, at least 93%, at least 94%, at least 95%, at least 96%, at least 97%, at least 98%, at least 99% or 100% pure.

Also provided by the invention are: (i) a non-naturally occurring and/or purified and/or engineered TCR which binds the target peptide:MHC, or a cell expressing and/or presenting such a TCR, for use in medicine, preferably in a method of treating cancer. The method may comprise adoptive therapy; (ii) the use of a TCR which binds the target peptide:MHC, or a cell expressing and/or presenting such a TCR, in the manufacture of a medicament for treating cancer; (iii) a method of treating cancer in a patient, comprising administering to the patient a TCR which binds the peptide:MHC target, or a cell expressing and/or presenting such a TCR. Therapeutic agents which may be associated with the TCRs of the invention include immunomodulators, radioactive compounds, enzymes (perforin for example) or chemotherapeutic agents (cis-platin for example). To ensure that toxic effects are exercised in the desired location the toxin could be inside a liposome linked to a TCR so that the compound is released slowly. This will prevent damaging effects during the transport in the body and ensure that the toxin has maximum effect after binding of the TCR to the relevant antigen presenting cells.

Other suitable therapeutic agents include small molecule cytotoxic agents, i.e. compounds with the ability to kill mammalian cells having a molecular weight of less than 700 Daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate glucuronate, auristatin E vincristine and doxorubicin; peptide cytotoxins, i.e. proteins or fragments thereof with the ability to kill mammalian cells. For example, ricin, diphtheria toxin, pseudomonas bacterial exotoxin A, DNase and RNase; radio-nuclides, i.e. unstable isotopes of elements which decay with the concurrent emission of one or more of a or b particles, or g rays. For example, iodine 131, rhenium 186, indium 111, yttrium 90, bismuth 210 and 213, actinium 225 and astatine 213; chelating agents may be used to facilitate the association of these radio-nuclides to the high affinity TCRs, or multimers thereof; immuno-stimulants, i.e. immune effector molecules which stimulate immune response. For example, cytokines such as IL-2 and IFN-g, Superantigens and mutants thereof; TCR-HLA fusions; chemokines such as IL-8, platelet factor 4, melanoma growth stimulatory protein, etc; antibodies or fragments thereof, including anti-T cell or NK cell determinant antibodies (e.g. anti-CD3, anti-CD28 or anti-CD16); alternative protein scaffolds with antibody like binding characteristics complement activators; xenogeneic protein domains, allogeneic protein domains, viral/bacterial protein domains, viral/bacterial peptides.

7.9. Methods of Use

Therapeutic TCRs may be used that specifically bind to antigen target or targets.

In vivo and/or in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. Effective doses may be extrapolated from dose-response curves derived from in vitro or animal model test systems.

An oligopeptide or polypeptide is within the scope of the invention if it has an amino acid sequence that is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to least one of the CDRs provided herein.

The terms "treatment," "treating," and the like are used herein to generally mean obtaining a desired pharmacologic and/or physiologic effect. The effect may be prophylactic, in terms of completely or partially preventing a disease, condition, or symptoms thereof, and/or may be therapeutic in terms of a partial or complete cure for a disease or condition and/or adverse effect, such as a symptom, attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms). Improvements in any conditions can be readily assessed according to standard methods and techniques known in the art. The population of subjects treated by the method of the disease includes subjects suffering from the undesirable condition or disease, as well as subjects at risk for development of the condition or disease.

By the term "therapeutically effective dose" or "effective amount" is meant a dose or amount that produces the desired effect for which it is administered. The exact dose or amount will depend on the purpose of the treatment, and will be ascertainable by one skilled in the art using known techniques (see, e.g., Lloyd (1999) The Art, Science and Technology of Pharmaceutical Compounding).

The term "sufficient amount" means an amount sufficient to produce a desired effect.

The term "therapeutically effective amount" is an amount that is effective to ameliorate a symptom of a disease. A therapeutically effective amount can be a "prophylactically effective amount" as prophylaxis can be considered therapy.

The term "ameliorating" refers to any therapeutically beneficial result in the treatment of a disease state, e.g., a neurodegenerative disease state, including prophylaxis, lessening in the severity or progression, remission, or cure thereof.

The actual amount administered, and rate and time-course of administration, will depend on the nature and severity of protein aggregation disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

In some embodiments, the pharmaceutical composition is administered by inhalation, orally, by buccal administration, by sublingual administration, by injection or by topical application.

In some embodiments, the pharmaceutical composition is administered in an amount sufficient to modulate survival of neurons or dopamine release. In some embodiments, the major cannabinoid is administered in an amount less than 1 g, less than 500 mg, less than 100 mg, less than 10 mg per dose.

In some embodiments, the pharmaceutical composition is administered once a day, 2-4 times a day, 2-4 times a week, once a week, or once every two weeks.

7.10. Examples

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1: Identification of Anti-Viral TCRs from Human Donor T Cell Repertoires Sourcing and Processing Human Materials De-identified peripheral blood mononuclear cells (PBMCs) in leukopaks were obtained from HLA-A*02:01 and HLA-A*24:02 healthy donors (AllCells), under a protocol approved by an Institutional Review Board (IRB). T cells were isolated from the PBMCs using the EasySep™ Human T Cell Enrichment Kit (Stemcell Technologies). Following isolation, T cells were cryopreserved using CryoStor® CS10 (Stemcell Technologies). For downstream single cell TCR□-TCR□ linkage, cells were thawed, washed, and resuspended at 5,000-6,000 cells per □l in cold DPBS+0.5% BSA with 12% OptiPrep™ Density Gradient Medium (Sigma). The resuspended cells were then used for microfluidic encapsulation as described in the next section.

Generating Paired TCRα-TCRβ Linkage Libraries

Library generation is divided into three steps: (i) poly(A)+ mRNA capture, (ii) multiplexed overlap extension reverse transcriptase polymerase chain reaction (OE-RT-PCR), and (iii) nested PCR to remove artifacts and add adapters for deep sequencing or expression libraries (Adler et al., 2017).

For poly(A)+ mRNA capture, we used a custom designed co-flow emulsion droplet microfluidic chip fabricated from glass (Dolomite). The microfluidic chip has two input channels for fluorocarbon oil (Dolomite), one input channel for the cell suspension mix, and one input channel for oligo-dT beads (New England Biolabs) in 0.5M NaCl, 0.5% Tween-20, and 20 mM DTT. The input channels are etched to 50 µm×150 µm for most of the chip's length, narrow to 55 µm at the droplet junction, and are coated with hydrophobic Pico-Glide (Dolomite). Three Mitos P-Pump pressure pumps (Dolomite) are used to pump the liquids through the chip. Droplet size depends on pressure, but typically we find that droplets of ~45 µm diameter are optimally stable. Emulsions were collected into 1.5 mL microcentrifuge tubes and incubated at 40° C. for 30 minutes to capture mRNA onto oligo-dT beads. Emulsions were then broken using Pico-Break (Dolomite) and mRNA-bound beads are magnetically isolated.

For multiplex OE-RT-PCR, mRNA-bound beads were re-encasuplated into droplets with an OE-RT-PCR mix. The OE-RT-PCR mix contains 2× one step RT-PCR buffer (ThermoFisher), 2.0 mM $MgSO_4$, SuperScript III reverse transcriptase (ThermoFisher), and Platinum Taq (ThermoFisher), plus a mixture of primers directed against the TRAC, TRBC, and all V-gene regions. TCR□ and TCR□ chains are physically linked by overlapping primer sequences included on the TRAC and TRBV primers. The amplified DNA was recovered from the droplets using a proprietary droplet breaking solution (GigaMune) and purified using a QIAquick PCR Purification Kit (Qiagen).

For nested PCR, the OE-RT-PCR product was first run on a 1.7% agarose gel and a band at 800-1200 bp was excised and purified using NucleoSpin Gel and PCR Clean-up Kit (Macherey-Nagel). Nested PCR was performed using NEBNext amplification mix (NEB) to add adapters for Illumina sequencing or cloning into a mammalian expression construct. PCR products were run on a 1.2% agarose gel, and the 800-1100 bp band was excised and purified using NucleoSpin Gel and PCR Clean-up Kit (Macherey-Nagel).

We ran 4 million live T cells from each of our six PBMC donors through this workflow to generate our six TCRαβ libraries.

Linked TCRαβ Repertoire Sequencing

Deep TCRαβ sequencing libraries were quantified using a quantitative PCR Illumina Library Quantification Kit (Kapa Biosystems) and diluted to 8.5-10 pM. Libraries were sequenced on a MiSeq (Illumina) using v3 600-cycle MiSeq Reagent Kits, according to the manufacturer's instructions. To identify the paired sequences from the TCRαβ libraries, we obtain forward reads of 357 cycles that cover the TCRα V gene and CDR3, and reverse reads of 162 cycles that cover the TCRβ CDR3 and enough of the TCRβ V gene for accurate calling.

To remove base call errors, we use the expected error filtering method of Edgar and Flyvbjerg (Edgar, *Bioinformatics* 2015, 31(21):3476-82). The expected number of errors (E) for a read is calculated from its Phred scores. By default, reads with E>1 are discarded, leaving reads for which the most probable number of base call errors is zero. For the clonotypes analyzed in this study, we excluded singletons and required that unique CDR3α+CDR3β paired sequences share the same V and J genes.

To identify reading frame and CDR3 amino acid sequences generated by V(D)J rearrangements, we first processed a database of well-curated TCR sequences (IMGT, http://www.imgt.org/download/LIGM-DB/; Lefranc et al., 2009) to generate position-specific sequence matrices (PSSMs) for the 5' and 3' CDR3 junctions. Each nucleotide sequence from the Illumina sequencing runs was translated into all reading frames. We then used the PSSMs to identify the FR3-CDR3 (5') and CDR3-FR4 (3') junctions and the appropriate protein reading frame for each of the nucleotide sequences. To report a CDR3 sequence, we required 5' and 3' PSSM hits in the same reading frame. Additionally, sequences that had low PSSM identity scores were marked with an exclamation point. These steps allowed us to predict valid, functional, CDR3 sequences with high confidence. We queried TCRα and TCRβ nucleotide sequences against the IMGT database of reference V and J gene germline sequences using UBLAST (https://www.drive5.com/usearch/manual/ublast_algo.html; Edgar, 2010); V and J genes were identified based on the UBLAST alignments with the best alignment (lowest E-values).

We used our massively parallel single cell droplet and sequencing technology to analyze the linked TCRαβ repertoires of three HLA-A*02:01 donors and three HLA-A*24:01 donors that were all seropositive for both cytomegalovirus (CMV) and Epstein-Barr virus (EBV).

Illumina sequencing error can be difficult to differentiate from bona fide TCRαβ sequence diversity (Shugay et al., 2014), so we applied conservative informatics to eliminate low-quality sequences. If we define TCRαβ clonotypes as sequences with unique combinations of CDR3α, CDR3β, and VJ genes, the libraries contained an average of 455,195 sequences (range: 339,707 to 721,521), for a total of 2,731,172 TCRαβ sequences. If we discard singletons, requiring at least 2 sequencing reads per clonotype, the TCRαβ libraries comprise an average of 141,588 TCRαβ sequences (range: 84,871 to 204,426), for a total of 849,525 TCRαβ sequences. The TCRαβ libraries were highly diverse, with the median clonotypes accounting for on average 0.00075% of the total sequencing reads. There were on average 1,912 different Vβ-Vα pairings (range: 1,772 to 2,036) in each repertoire. In sum, the repertoires spanned a total of 2,160 different Vβ-Vα pairings, with a wide range of frequencies.

Single Chain TCRα and TCRβ Repertoire Sequencing

For single chain sequencing of the recombinant TCRα-TCRβ expression libraries, TCRα and TCRβ V(D)J regions were amplified separately using universal primers, that contained adapters for Illumina sequencing, within the TRAV.SS and TRAC regions for TCRα and within the TRBV.SS and TRBC regions for TCRβ. We conducted RT-PCR off RNA samples using SuperScript III reverse transcriptase (ThermoFisher) and Platinum Taq (ThermoFisher). We used NEBNext amplification mix (NEB) for PCR off plasmid DNA. These amplicons were run on 1.7% agarose gels and the 500-600 bp band was excised and purified using NucleoSpin Gel and PCR Clean-up Kit (Macherey-Nagel). Samples were separately quantified using an Illumina Library Quantification Kit (Kapa Biosystems). After diluting to 9 pM, libraries were sequenced on a MiSeq (Illumina) using v2 500-cycle MiSeq Reagent Kits, according to the manufacturer's instructions. We obtained overlapping forward and reverse reads of 255 cycles for TCRα and TCRβ separately. TCRα and TCRβ sequences were analyzed separately using the same methods as described above for paired sequences, with the additional requirement that overlapping reads were observed.

Generating Recombinant TCRαβ Jurkat Expression Libraries

We developed a subcloning workflow to convert the linked TCRαβ amplicons into full-length lentiviral expression constructs. In this workflow, we first used nested PCR to add overhang adapters to the 5' and 3' ends of the linked TCRαβ amplicons for downstream Gibson assembly. Then, we used NEBuilder HiFi DNA Assembly Master Mix (New England Biolabs) to insert the linked TCRαβ library into a pReceiver-based lentiviral vector (GeneCopoeia) that contains the EF1α promoter, a TCRα signal sequence, the TCRβ constant region, and the Puromycin resistance gene. We transformed this intermediate library into Endura electrocompetent E. coli (Lucigen), plated onto LB Lennox carbenicillin plates (Teknova), and scraped and pooled >5 million colonies from each library for plasmid purification. Plasmids were purified using the endotoxin free ZymoPURE II Plasmid Maxiprep Kit (Zymo Research). These intermediate libraries were linearized with a NheI-HF (New England Biolabs) restriction digest present within the linker region, run on a 0.8% agarose gel, and gel extracted using the NucleoSpin Gel and PCR Clean-up Kit (Macherey-Nagel). To create the full-length TCRαβ lentiviral libraries, we performed a second Gibson assembly to insert the TCRα constant region, a ribosomal skip motif (P2A; Funston, Journal General Virology 2008, 89(Pt 2):389-96), and a TCRβ signal sequence. These full-length TCRαβ lentiviral libraries were transformed into Endura electrocompetent cells and purified using the endotoxin free maxiprep kit as described above.

Engineering Human CD8 Expressing Jurkat Cells

To screen our natively paired TCRαβ libraries for TCRs reactive to MHC-class I presented peptides, we engineered the TCRβ deficient (ΔTCRβ) Jurkat cell line J.RT3-T3.5 (ATCC TIB-153) to stably express human CD8 (Lyons, Cancer Immunol Immunother 2006, 55(9):1142-50). We built a lentiviral vector with the PGK promoter driving expression of human CD8A, a P2A ribosomal skip motif, CD8B(M-1) (Thakral D, et al, J Immunol 2008, 180(11):7431-42), and an IRES-Blasticidin resistance gene cassette in the pReceiver (GeneCopoeia) backbone. Lentivirus was packaged and transduced into TCRβ deficient Jurkat cells as described below. Blasticidin selection was started on day two post-transduction and continued for 14 days to select for stable integration. CD8 surface expression was confirmed by flow cytometry and this CD8+ΔTCRβ Jurkat cell line was cryopreserved for future use.

Lentiviral Transduction of Jurkat Cells

We then optimized our lentiviral transduction protocol to obtain a low transduction efficiency to ensure that we expressed only one TCRαβ pair per cell. We packaged lentivirus into VSV-G pseudotyped lentiviral particles using the $3^{rd}$ generation ViraSafe Lentiviral Packaging System (Cell Biolabs) and Lenti-Pac 293Ta cells (GeneCopoeia). 21 million Lenti-Pac 293Ta cells per 10 cm plate were transfected with 4.3 ug pCMV-VSV-G, 4.3 ug pRSV-Rev, 4.3 ug pCgpV, and 4.3 ug of the TCRαβ expression libraries using Lipofectamine 3000 (ThermoFisher) following the manufacturer's protocol. Lentiviral supernatant was collected at 48 hours post-transfection, spun down at 500×g for 10 minutes to eliminate cellular debris, and clarified through a 0.45 um syringe filter. RNA was isolated from fresh lentiviral supernatant using the NucleoSpin RNA Virus kit (Macherey-Nagel) following the manufacturer's protocol. Fresh lentiviral supernatant was used to transduce CD8$^+$ΔTCRβ Jurkat cells. Clarified lentiviral supernatant was added at a 1:10 ratio with Jurkat cells in RPMI media with 10% FBS and 8 ug/ml Polybrene (EMD Millipore). Jurkat cells were incubated with lentiviral particles for 6 hours and then media was exchanged. Two days after viral transduction, Jurkat cells were analyzed for cell surface CD3 and TCRαβ expression to measure viral transduction efficiency. Cells were then cultured for 14 days with puromycin to select for stable integration and again assessed for CD3 and TCRαβ surface expression. To generate the natively paired TCRαβ Jurkat expression libraries, we transduced 40 million CD8$^+$ ΔTCRβ Jurkat and on day 2 observed surface expression on 8-14% of transduced cells compared to 4% on the parental Jurkat cells. TCRαβ surface increased to 42-56% following selection. For monoclonal TCRαβ cell line generation, 800,000 CD8+ΔTCRβ Jurkat cells were transduced and selected with puromycin for 14 days. CD3 and TCRαβ surface expression was measured following selection.

Screening Recombinant TCRαβ Jurkat Libraries

We screened the TCRαβ Jurkat libraries with peptide-HLA (pHLA) dextramers (Immudex) targeting common viral antigens from CMV and EBV. We stained 2-5 million CD8+TCRαβ Jurkat library cells with 10 ul of APC-conjugated dextramer at room temperature for 10 minutes. Cells were then stained with an anti-CD3-FITC antibody (clone: UCHT1; BioLegend) for 30 minutes at 4° C. and DAPI (BioLegend) to assess cell viability. Cells were then sorted on a FACSMelody (BD Biosciences) for Live CD3$^+$/dextramer$^+$ cells. The sorted Jurkat cells were recovered and expanded in RPMI media with 10% FBS and 100 U/ml Pen/Strep (Gibco). Once cells reached high viability (>85%) and appropriate cell numbers, 2 million cells were lysed, and RNA was extracted using the NucleoSpin RNA Plus kit (Macherey-Nagel) for single chain TCRα and TCRβ repertoire sequencing as described above. Multiple rounds of dextramer staining, FACS sorting, and cell expansion were conducted to enrich for populations of pHLA-binding TCRs.

Following pHLA-binding enrichment, we co-cultured CD8$^+$ TCRαβ Jurkat cell populations with peptide-pulsed antigen presenting cells (APCs) to assess cell activation. We pulsed T2 cells with 10 μM peptide, mixed 200,000 peptide-pulsed T2 cells with 200,000 CD8$^+$ TCRαβ Jurkat cells per well in 96-well round-bottom plates (Falcon), and cultured for 16-20 hours. Cells were harvested out of the round-bottom plates and stained for HLA-A2 (clone: BB7.2; BioLegend), CD69 (clone: FN50; BioLegend), CD62L (clone: DREG-56; Bio-Legend), and cell viability with DAPI. Cells were analyzed on a FACSMelody or CytoFLEX LX (Beckman Coulter) for activation (HLA-A2-/CD69+/CD62L-). We used 1× Cell Stimulation Cocktail (eBioscience, ThermoFisher) as a positive control and irrelevant peptide-pulsed T2 cells as a negative control. T2 cells natively express HLA-A*02:01, and we generated a stable T2 cell line that expresses HLA-A*24:02 and GFP (data not shown) for additional peptide presentation. To identify TCRs present in peptide-activated Jurkat cells, we co-cultured partially enriched TCRαβ Jurkat cell populations with peptide-pulsed T2 cells, stained with the activation markers described above and sorted for activated (HLA-A2-/CD69+/CD62L-) cells on a FACSMelody. These activated cells were lysed and RNA isolated using the Nucleo-Spin RNA Plus XS kit (Macherey-Nagel) for single chain TCRα and TCRβ repertoire sequencing. Peptides were synthesized at >90% purity (ELIM Biopharm), resuspended in DMSO to 4 mg/ml, aliquoted for single use, and stored at −20° C.

To identify virus-specific TCRαβ clones, we stained 2-5 million TCR-Jurkat cells with fluorescently labeled MHC dextramers against five well-characterized peptide:MHC targets: HLA-A*02:01 CMV pp65(NLV), HLA-A*02:01 CMV IE-1(VLE), HLA-A*02:01 EBV BMLF1(GLC), HLA-A*02:01 EBV LMP2(CLG), and HLA-A*24:02 EBV LMP2(TYG). All three of the HLA-A*02:01 donors yielded putative binder clones, with Donor CSS-930 yielding clones against all four HLA-A*02:01 targets. Donor CSS-948 showed some putative binders against HLA-A*24:02 EBV LMP2(TYG). In general, TCRαβ clones directed against the peptide:MHC targets were rare, ranging from 0.02-0.14% of the cells in the TCR-Jurkat repertoires. In parallel, we stained 1-3 million primary PBMC T cells from the same donors and found similar frequencies of virus-specific cells (range: 0.055-0.32%). Unlike primary PBMC T cells, Jurkat cells are easy to culture and expand indefinitely. This feature enables us to expand the "Round 1 dextramer" cells, re-stain with dextramer, and sort a second time ("Round 2 dextramer"), an approach which we term "panning", as for phage display (McCafferty et al., 1990). To test the method, we first performed control experiments with a previously reported HLA-A*02:01 human MART-1 TCRαβ clone spiked in at a range of 0.001-1% frequencies Panning recovered the clone quantitatively across all levels tested. We panned the six TCR-Jurkat libraries against the five peptide:MHC virus targets Panning increased oligoclonality considerably, generating top 20 median clone frequencies of 64.6% after the Round 2 sorts (range: 16.2-21.8%), 94.3% after the Round 3 sorts (range: 44.1-88.9%), and 97.1% after the Round 4 sorts (range: 95.4-98.6%). In one case (Donor CSS-944), a single pp65(NLV) clone comprised >95% of the Round 4 sort.

Because FACS never achieves 100% specificity and 100% sensitivity, we assumed that panning would result in both bona fide and false-positive TCRαβ clones. TCRαβ clones present a relatively high frequencies in the initial repertoires are more likely to appear as false positives. With this issue in mind, we identified twenty-four TCRαβ clones that were >10-fold enriched between the original repertoire and the last round of panning. The median enrichment for these TCRαβ clones was 6,480-fold, with two TCRαβ clones enriched more than one million-fold. The clones were generally very rare in the initial repertoires (median: 0.035%), with one TCRαβ clone initially present at 0.000035% of the initial repertoire.

Therapeutically relevant TCRs should activate T cells upon binding their cognate peptide:MHC, but prior work has established that TCRs can bind their peptide:MHC target but fail to activate T cells (Sibener et al., *Cell* 2018, 174(3): 672-687.e27). Thus, to further reduce false positives, we performed in vitro activation screens on MHC dextramer-enriched TCRαβ Jurkat populations Panning Round 2, 3, or 4 TCR-Jurkat populations were incubated with peptide-pulsed T2 cells, and then FACS-selected for increased cell surface CD69 and decreased CD62L expression. The ratio of the frequency of a TCR in the CD69+/CD62L− fraction to its frequency in the CD69−/CD62L+ fraction was used to quantify the TCR's ability to activate T cells. Activation ratios were integrated with corresponding TCRαβ read frequencies after the $3^{rd}$ or $4^{th}$ round of MHC dextramer panning, to assess the likelihood of a true positive. The median activation ratio was 0.53, suggesting that the majority of the MHC dextramer-panned TCRs were false positives. However, 10/24 of the TCRαβ clones that were highly enriched by MHC dextramer panning also had activation ratios of >0.9.

Monoclonal TCRαβ Characterization

Enriched TCRα and TCRβ single chain sequences were identified from the pHLA-binding and cell activation screens. We used this enrichment data and the natively paired TCRα-TCRβ sequencing data to identify candidate antigen-reactive TCR clones. We designed full-length TCRα-TCRβ lentiviral expression constructs using the Illumina sequencing data, specifically the CDR3 nucleotide sequences and V-gene calls, and synthesized these plasmids using the BioXp 3200 system (SGI-DNA). These monoclonal TCRαβ expression constructs follow the same layout as the TCRαβ libraries. Lentiviral plasmids were sequence verified by Sanger sequencing, packaged into VSV-G pseudotyped lentiviral particles, transduced into CD8+ ΔTCRβ Jurkat cells, and stable cell lines were selected.

Monoclonal CD8+ TCRαβ Jurkat cell lines were assessed for pHLA binding and cellular activation. We stained 0.5-1 million cells with 5 ul of pHLA dextramer and anti-CD3 antibodies as described above. We then ran co-culture assays with the monoclonal CD8+ TCRαβ Jurkat cell lines that showed pHLA binding. As described above, we pulsed T2 cells with 1004 peptide, mixed 200,000 peptide-pulsed T2 cells with 200,000 TCRαβ Jurkat cells per well, and measured cell activation by staining for CD69 and CD62L.

We then measured functional avidity of the monoclonal TCRs that showed cellular activation using T2 cells pulsed with a dilution series of peptide (1E-7-10 μM). Cells were co-cultured in duplicate wells for 20 hours, harvested, pooled, and stained for activation markers as described above. Cells were run on the CytoFLEX LX and Jurkat cell CD69 Median Fluorescence Intensity (MFI) was calculated using FlowJo (Treestar) and analyzed in Prism (GraphPad). Two independent experiments were conducted, and the mean and standard deviation values were plotted.

Finally, we analyzed a set of antigen-reactive TCRs for peptide specificity using alanine scanning mutagenesis as previously described (Chheda Z S, *Journal of Exp Med* 2018, 215(1):141-157). Synthetic peptides with alanine substitutions were obtained from Pepscan (purity:crude), resuspended in DMSO to 5 mg/ml, aliquoted, and stored at −20° C. T2 cells were pulsed with 10 μg/ml of peptide and co-cultured with monoclonal CD8+ TCRαβ Jurkat cell lines for 24 hours as described above. Following co-culture, cell supernatant was removed and stored at −80° C. IL-2 levels were measured in cell supernatant by sandwich ELISA (BioLegend) following the manufacturer's protocol. MaxiSorp ELISA plates were coated with antibody at 4° C. overnight. ELISA wells were blocked with PBS+1% BSA, 50 μl of cell supernatant was added to duplicate wells and incubated at room temperature for 2 hours, and IL-2 levels were measured using an anti-IL-2 detection antibody followed by Avidin-HRP incubation and signal development with aTMB substrate solution. Signal absorbanse was read at 450 nm on a SpectraMax i3x (Molecular Devices). IL-2 levels were calculated using a standard curve run on the same plate. Two independent experiments were conducted; mean and standard deviation values were plotted in Prism (GraphPad). Generally, peptides with alanine mutations induced lower IL-2 secretion than wild type cognate peptides, and irrelevant peptides did not induce IL-2 secretion. The data provided some evidence of contact residues, which varied between TCRs and peptide:MHC targets.

TABLE 4

Funtional annotation of TCR sequences

| Target | Library Binding | Library Activation | Monoclonal Binding | Monoclonal Activation | TCR number |
|---|---|---|---|---|---|
| A2/pp65(NLV) | Yes | No | No (weak expression) | Not tested | 1 |
| A2/pp65(NLV) | Yes | No | Yes | No | 2 |
| A2/pp65(NLV) | Yes | No | No | Not tested | 3 |
| A2/pp65(NLV) | Yes | No | No | Not tested | 4 |
| A2/pp65(NLV) | Enriched but background binding | No | No | Not tested | 5 |
| A2/pp65(NLV) | Enriched but background binding | No | No | Not tested | 6 |
| A2/pp65(NLV) | Enriched but background binding | No | No | Not tested | 7 |
| A2/pp65(NLV) | Yes | Yes | Yes | Yes | 8 |
| A2/pp65(NLV) | Yes | No | Yes | No | 9 |
| A2/pp65(NLV) | Yes | Yes | Yes | No | 10 |
| A2/pp65(NLV) | No | No | No | Not tested | 11 |
| A2/pp65(NLV) | No | No | No | Not tested | 12 |
| A2/pp65(NLV) | No | No | No | Not tested | 13 |
| A2/pp65(NLV) | No | No | No | Not tested | 14 |
| A2/IE-1(VLE) | Yes | Yes | Yes | Yes | 15 |
| A2/IE-1(VLE) | Yes | No | No | Not tested | 16 |
| A2/IE-1(VLE) | Yes | No | No (weak expression) | Not tested | 17 |
| A2/IE-1(VLE) | Yes | No | No | Not tested | 18 |
| A2/BMLF1(GLC) | Yes | Yes | Yes | Yes | 19 |
| A2/BMLF1(GLC) | Yes | No | No | Not tested | 20 |
| A2/BMLF1(GLC) | Yes | No | No | Not tested | 21 |
| A2/BMLF1(GLC) | Yes | No | No | Not tested | 22 |
| A2/BMLF1(GLC) | Yes (weak) | No | Slight binding (weak expression) | Slight activation (weak expression) | 23 |

TABLE 4-continued

Funtional annotation of TCR sequences

| Target | Library Binding | Library Activation | Monoclonal Binding | Monoclonal Activation | TCR number |
|---|---|---|---|---|---|
| A2/BMLF1(GLC) | Yes | Yes | Yes (weak) | Yes | 24 |
| A2/BMLF1(GLC) | Yes | No | No | Not tested | 25 |
| A2/BMLF1(GLC) | Yes | No | No | Not tested | 26 |
| A2/BMLF1(GLC) | Enriched but background binding | No | No (weak expression) | Not tested | 27 |
| A2/BMLF1(GLC) | Enriched but background binding | No | No | Not tested | 28 |
| A2/LMP2(CLG) | Yes | Yes | Yes | Yes | 29 |
| A2/LMP2(CLG) | Yes | No | No | Not tested | 30 |
| A2/LMP2(CLG) | Yes | No | No | Not tested | 31 |
| A2/LMP2(CLG) | Yes | Yes | Yes (weak) | Yes | 32 |
| A2/LMP2(CLG) | Yes (weak) | No | No | Not tested | 33 |
| A2/LMP2(CLG) | Yes | Yes | No | No | 34 |
| A2/LMP2(CLG) | Yes (weak) | Yes | Yes (weak) | Yes | 35 |
| A2/LMP2(CLG) | Yes | Yes | No | No | 36 |
| A2/LMP2(CLG) | Yes | Yes | No | No | 37 |
| A24/LMP2(TYG) | Yes | Target and irrelevant peptide activated | Yes? (very weak) | Yes | 40 |
| A24/LMP2(TYG) | Little to no enrichment | No | No | Not tested | 41 |
| A24/LMP2(TYG) | Yes | No | No | Not tested | 42 |

8. INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

9. EQUIVALENTS

Whereas various specific embodiments have been illustrated and described, the above specification is not restrictive. It will be appreciated that various changes can be made without departing from the spirit and scope of the invention(s). Many variations will become apparent to those skilled in the art upon review of this specification.

The invention claimed is:

1. A method of identifying anti-viral T cell receptors specific to a viral peptide, comprising:
   providing primary T cells from at least one human donor;
   isolating individual primary T cells from the at least one human donor in droplets;
   isolating poly(A)+ mRNA transcripts by capture from the isolated primary T cells;
   generating by OE-RT-PCR a paired TCRα-TCRβ linkage library comprising linked TCRαβ amplicons from the isolated poly(A)+ mRNA transcripts;
   performing nested PCR;
   converting said linked TCRαβ amplicons into expression constructs for expression of full-length TCRαβ;
   introducing said expression constructs into a plurality of host cells;
   inducing expression of recombinant T cell receptors from said expression constructs in said plurality of host cells, thereby generating a full-length TCRαβ expression library;
   enriching a first subset of the plurality of host cells in the full-length TCRαβ expression library based on their binding property to a soluble complex comprising WIC and the peptide;
   exposing said first subset of the plurality of host cells to peptide-pulsed antigen-presenting cells;

selecting a second subset of the host cells from the first subset of the host cells by detecting expression of activation markers; and sequencing transcripts of TCRα and TCRβ isolated from the second subset of the host cells, thereby identifying T cell receptors specific to the peptide.

2. The method of claim 1, wherein the activation markers are selected from the group consisting of CD69 and CD62L.

3. The method of claim 1, wherein the second subset of the host cells are selected for being CD69+ and CD62L−.

4. The method of claim 1, wherein the selecting step is performed by cell sorting using the activation markers.

5. The method of claim 1, wherein the enriching step is performed by cell sorting detecting binding of the first subset of the plurality of host cells to the soluble complex.

6. The method of claim 1, wherein the peptide is from a pathogen.

7. The method of claim 1, wherein the at least one mammalian donor has been exposed to the virus.

8. The method of claim 1, wherein the virus is CMV or EBV.

9. The method of claim 1, wherein the soluble complex is a dextramer.

10. The method of claim 1, wherein the antigen presenting cells are T2 cells.

11. The method of claim 1, wherein the host cells are CD8+ Jurkat cells.

12. The method of claim 1, wherein the primary immune cells express CD4 or CD8.

13. The method of claim 1, wherein the recombinant T cell receptor library comprises at least 100 unique recombinant T cell receptor expression constructs.

14. The method of claim 13, wherein the recombinant T cell receptor library comprises at least 1,000 unique recombinant T cell receptor expression constructs.

* * * * *

UNITED STATES PATENT AND TRADEMARK OFFICE
CERTIFICATE OF CORRECTION

PATENT NO. : 11,421,220 B2
APPLICATION NO. : 17/480697
DATED : August 23, 2022
INVENTOR(S) : Spindler et al.

Page 1 of 1

It is certified that error appears in the above-identified patent and that said Letters Patent is hereby corrected as shown below:

On the Title Page

In Column 1, item (73), under Assignee, Line 1, delete "San Francisco, CA" and insert -- South San Francisco, CA --, therefor.

In the Claims

In Column 96, Claim 1, Line 63, delete "WIC" and insert -- MHC --, therefor.

Signed and Sealed this
Twenty-second Day of August, 2023

*Katherine Kelly Vidal*

Katherine Kelly Vidal
*Director of the United States Patent and Trademark Office*

```
                       SEQUENCE LISTING

<160> NUMBER OF SEQ ID NOS: 84

<210> SEQ ID NO 1
<211> LENGTH: 112
<212> TYPE: PRT
<213> ORGANISM: Homo sapiens
<220> FEATURE:
<223> OTHER INFORMATION: alpha variable chain for T cell receptor 1

<400> SEQUENCE: 1

Ala Gln Ser Val Thr Gln Leu Asp Ser Gln Val Pro Val Phe Glu Glu
1               5                   10                  15

Ala Pro Val Glu Leu Arg Cys Asn Tyr Ser Ser Val Ser Val Tyr
            20                  25                  30

Leu Phe Trp Tyr Val Gln Tyr Pro Asn Gln Gly Leu Gln Leu Leu Leu
            35                  40                  45

Lys Tyr Leu Ser Gly Ser Thr Leu Val Lys Gly Ile Asn Gly Phe Glu
    50                  55                  60

Ala Glu Phe Asn Lys Ser Gln Thr Ser Phe His Leu Arg Lys Pro Ser
65                  70                  75                  80

Val His Ile Ser Asp Thr Ala Glu Tyr Phe Cys Ala Val Glu Ser Gly
                85                  90                  95

Asp Tyr Lys Leu Ser Leu Gly Ala Gly Thr Thr Val Thr Val Arg Ala
            100                 105                 110
```

```
<210> SEQ ID NO 2
<211> LENGTH: 114
<212> TYPE: PRT
<213> ORGANISM: Homo sapiens
<220> FEATURE:
<223> OTHER INFORMATION: beta variable chain for T cell receptor 1

<400> SEQUENCE: 2

Ser Ala Val Ile Ser Gln Lys Pro Arg Asp Ile Cys Gln Arg Gly
1               5                   10                  15

Thr Ser Leu Thr Ile Gln Cys Gln Val Asp Ser Gln Val Thr Met Met
            20                  25                  30

Phe Trp Tyr Arg Gln Gln Pro Gly Gln Ser Leu Thr Leu Ile Ala Thr
        35                  40                  45

Ala Asn Gln Gly Ser Glu Ala Thr Tyr Glu Ser Gly Phe Val Ile Asp
    50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser Val Pro
                85                  90                  95

Gly Arg Leu Asn Thr Glu Ala Phe Phe Gly Gln Gly Thr Arg Leu Thr
            100                 105                 110

Val Val

<210> SEQ ID NO 3
<211> LENGTH: 111
<212> TYPE: PRT
<213> ORGANISM: Homo sapiens
<220> FEATURE:
<223> OTHER INFORMATION: alpha variable chain for T cell receptor 2

<400> SEQUENCE: 3

Arg Lys Glu Val Glu Gln Asp Pro Gly Pro Phe Asn Val Pro Glu Gly
1               5                   10                  15

Ala Thr Val Ala Phe Asn Cys Thr Tyr Ser Asn Ser Ala Ser Gln Ser
            20                  25                  30

Phe Phe Trp Tyr Arg Gln Asp Cys Arg Lys Glu Pro Lys Leu Leu Met
        35                  40                  45

Ser Val Tyr Ser Ser Gly Asn Glu Asp Gly Arg Phe Thr Ala Gln Leu
    50                  55                  60

Asn Arg Ala Ser Gln Tyr Ile Ser Leu Leu Ile Arg Asp Ser Lys Leu
65                  70                  75                  80

Ser Asp Ser Ala Thr Tyr Leu Cys Val Val Asn Pro Thr Gly Gly Phe
                85                  90                  95

Gln Lys Leu Val Phe Gly Thr Gly Thr Arg Leu Leu Val Ser Pro
            100                 105                 110

<210> SEQ ID NO 4
<211> LENGTH: 113
<212> TYPE: PRT
<213> ORGANISM: Homo sapiens
<220> FEATURE:
<223> OTHER INFORMATION: beta variable chain for T cell receptor 2

<400> SEQUENCE: 4

Asn Ala Gly Val Thr Gln Thr Pro Lys Phe Arg Val Leu Lys Thr Gly
1               5                   10                  15

Gln Ser Met Thr Leu Leu Cys Ala Gln Asp Met Asn His Glu Tyr Met
            20                  25                  30
```

```
Tyr Trp Tyr Arg Gln Asp Pro Gly Met Gly Leu Arg Leu Ile His Tyr
        35                  40                  45

Ser Val Gly Glu Gly Thr Thr Ala Lys Gly Glu Val Pro Asp Gly Tyr
 50                  55                  60

Asn Val Ser Arg Leu Lys Lys Gln Asn Phe Leu Leu Gly Leu Glu Ser
 65                  70                  75                  80

Ala Ala Pro Ser Gln Thr Ser Val Tyr Phe Cys Ala Ser Ser Tyr Phe
                 85                  90                  95

Ser Gly Pro Tyr Glu Gln Tyr Phe Gly Pro Gly Thr Arg Leu Thr Val
                100                 105                 110

Thr
```

<210> SEQ ID NO 5
<211> LENGTH: 111
<212> TYPE: PRT
<213> ORGANISM: Homo sapiens
<220> FEATURE:
<223> OTHER INFORMATION: alpha variable chain for T cell receptor 3

<400> SEQUENCE: 5

```
Gln Lys Glu Val Glu Gln Asn Ser Gly Pro Leu Ser Val Pro Glu Gly
 1               5                  10                  15

Ala Ile Ala Ser Leu Asn Cys Thr Tyr Ser Asp Arg Gly Ser Gln Ser
                 20                  25                  30

Phe Phe Trp Tyr Arg Gln Tyr Ser Gly Lys Ser Pro Glu Leu Ile Met
        35                  40                  45

Phe Ile Tyr Ser Asn Gly Asp Lys Glu Asp Gly Arg Phe Thr Ala Gln
 50                  55                  60

Leu Asn Lys Ala Ser Gln Tyr Val Ser Leu Leu Ile Arg Asp Ser Gln
 65                  70                  75                  80

Pro Ser Asp Ser Ala Thr Tyr Leu Cys Ala Val His Thr Gly Thr Ala
                 85                  90                  95

Ser Lys Leu Thr Phe Gly Thr Gly Thr Arg Leu Gln Val Thr Leu
                100                 105                 110
```

<210> SEQ ID NO 6
<211> LENGTH: 113
<212> TYPE: PRT
<213> ORGANISM: Homo sapiens
<220> FEATURE:
<223> OTHER INFORMATION: beta variable chain for T cell receptor 3

<400> SEQUENCE: 6

```
Glu Ala Gln Val Thr Gln Asn Pro Arg Tyr Leu Ile Thr Val Thr Gly
 1               5                  10                  15

Lys Lys Leu Thr Val Thr Cys Ser Gln Asn Met Asn His Glu Tyr Met
                 20                  25                  30

Ser Trp Tyr Arg Gln Asp Pro Gly Leu Gly Leu Arg Gln Ile Tyr Tyr
        35                  40                  45

Ser Met Asn Val Glu Val Ala Asp Lys Gly Asp Val Pro Glu Gly Tyr
 50                  55                  60

Lys Val Pro Arg Lys Glu Lys Arg Asn Phe Pro Leu Ile Leu Glu Ser
 65                  70                  75                  80

Pro Ser Pro Asn Gln Thr Ser Leu Tyr Phe Cys Ala Ser Ser Leu Gln
                 85                  90                  95

Gly Pro Asn Thr Glu Ala Phe Phe Gly Gln Gly Thr Arg Leu Thr Val
                100                 105                 110
```

Val

<210> SEQ ID NO 7
<211> LENGTH: 109
<212> TYPE: PRT
<213> ORGANISM: Homo sapiens
<220> FEATURE:
<223> OTHER INFORMATION: alpha variable chain for T cell receptor 4

<400> SEQUENCE: 7

Gln Lys Glu Val Glu Gln Asp Pro Gly Pro Leu Ser Val Pro Glu Gly
1               5                   10                  15

Ala Ile Val Ser Leu Asn Cys Thr Tyr Ser Asn Ser Ala Phe Gln Tyr
            20                  25                  30

Phe Met Trp Tyr Arg Gln Tyr Ser Arg Lys Gly Pro Glu Leu Leu Met
        35                  40                  45

Tyr Thr Tyr Ser Ser Gly Asn Lys Glu Asp Gly Arg Phe Thr Ala Gln
    50                  55                  60

Val Asp Lys Ser Ser Lys Tyr Ile Ser Leu Phe Ile Arg Asp Ser Gln
65                  70                  75                  80

Pro Ser Asp Ser Ala Thr Tyr Leu Cys Ala Met Arg Gly Thr Tyr Lys
                85                  90                  95

Tyr Ile Phe Gly Thr Gly Thr Arg Leu Lys Val Leu Ala
            100                 105

<210> SEQ ID NO 8
<211> LENGTH: 112
<212> TYPE: PRT
<213> ORGANISM: Homo sapiens
<220> FEATURE:
<223> OTHER INFORMATION: beta variable chain for T cell receptor 4

<400> SEQUENCE: 8

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Met Met Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Ser Phe
                85                  90                  95

Ser Ser Tyr Glu Gln Tyr Phe Gly Pro Gly Thr Arg Leu Thr Val Thr
            100                 105                 110

<210> SEQ ID NO 9
<211> LENGTH: 112
<212> TYPE: PRT
<213> ORGANISM: Homo sapiens
<220> FEATURE:
<223> OTHER INFORMATION: alpha variable chain for T cell receptor 5

<400> SEQUENCE: 9

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn

```
                    20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
 50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Pro Gly Gly Gly
                85                  90                  95

Ala Asp Gly Leu Thr Phe Gly Lys Gly Thr His Leu Ile Ile Gln Pro
                100                 105                 110

<210> SEQ ID NO 10
<211> LENGTH: 112
<212> TYPE: PRT
<213> ORGANISM: Homo sapiens
<220> FEATURE:
<223> OTHER INFORMATION: beta variable chain for T cell receptor 5

<400> SEQUENCE: 10

Asp Ala Gly Val Ile Gln Ser Pro Arg His Glu Val Thr Glu Met Gly
 1               5                  10                  15

Gln Glu Val Thr Leu Arg Cys Lys Pro Ile Ser Gly His Asp Tyr Leu
                20                  25                  30

Phe Trp Tyr Arg Gln Thr Met Met Arg Gly Leu Glu Leu Leu Ile Tyr
            35                  40                  45

Phe Asn Asn Asn Val Pro Ile Asp Asp Ser Gly Met Pro Glu Asp Arg
 50                  55                  60

Phe Ser Ala Lys Met Pro Asn Ala Ser Phe Ser Thr Leu Lys Ile Gln
 65                  70                  75                  80

Pro Ser Glu Pro Arg Asp Ser Ala Val Tyr Phe Cys Ala Ser Ser Arg
                85                  90                  95

Gln Trp Glu Thr Gln Tyr Phe Gly Pro Gly Thr Arg Leu Leu Val Leu
                100                 105                 110

<210> SEQ ID NO 11
<211> LENGTH: 113
<212> TYPE: PRT
<213> ORGANISM: Homo sapiens
<220> FEATURE:
<223> OTHER INFORMATION: alpha variable chain for T cell receptor 6

<400> SEQUENCE: 11

Ala Gln Ser Val Ala Gln Pro Glu Asp Gln Val Asn Val Ala Glu Gly
 1               5                  10                  15

Asn Pro Leu Thr Val Lys Cys Thr Tyr Ser Val Ser Gly Asn Pro Tyr
                20                  25                  30

Leu Phe Trp Tyr Val Gln Tyr Pro Asn Arg Gly Leu Gln Phe Leu Leu
            35                  40                  45

Lys Tyr Ile Thr Gly Asp Asn Leu Val Lys Gly Ser Tyr Gly Phe Glu
 50                  55                  60

Ala Glu Phe Asn Lys Ser Gln Thr Ser Phe His Leu Lys Lys Pro Ser
 65                  70                  75                  80

Ala Leu Val Ser Asp Ser Ala Leu Tyr Phe Cys Ala Val Arg Ala Ser
                85                  90                  95

Tyr Gly Gln Asn Phe Val Phe Gly Pro Gly Thr Arg Leu Ser Val Leu
                100                 105                 110
```

Pro

<210> SEQ ID NO 12
<211> LENGTH: 114
<212> TYPE: PRT
<213> ORGANISM: Homo sapiens
<220> FEATURE:
<223> OTHER INFORMATION: beta variable chain for T cell receptor 6

<400> SEQUENCE: 12

Asp Ala Gly Ile Thr Gln Ser Pro Arg His Lys Val Thr Glu Thr Gly
1               5                   10                  15

Thr Pro Val Thr Leu Arg Cys His Gln Thr Glu Asn His Arg Tyr Met
            20                  25                  30

Tyr Trp Tyr Arg Gln Asp Pro Gly His Gly Leu Arg Leu Ile His Tyr
        35                  40                  45

Ser Tyr Gly Val Lys Asp Thr Asp Lys Gly Glu Val Ser Asp Gly Tyr
    50                  55                  60

Ser Val Ser Arg Ser Lys Thr Glu Asp Phe Leu Leu Thr Leu Glu Ser
65                  70                  75                  80

Ala Thr Ser Ser Gln Thr Ser Val Tyr Phe Cys Ala Ile Ser Glu Arg
                85                  90                  95

Gly Gly Thr Asn Thr Glu Ala Phe Phe Gly Gln Gly Thr Arg Leu Thr
            100                 105                 110

Val Val

<210> SEQ ID NO 13
<211> LENGTH: 115
<212> TYPE: PRT
<213> ORGANISM: Homo sapiens
<220> FEATURE:
<223> OTHER INFORMATION: alpha variable chain for T cell receptor 7

<400> SEQUENCE: 13

Ala Gln Ser Val Ala Gln Pro Glu Asp Gln Val Asn Val Ala Glu Gly
1               5                   10                  15

Asn Pro Leu Thr Val Lys Cys Thr Tyr Ser Val Ser Gly Asn Pro Tyr
            20                  25                  30

Leu Phe Trp Tyr Val Gln Tyr Pro Asn Arg Gly Leu Gln Phe Leu Leu
        35                  40                  45

Lys Tyr Ile Thr Gly Asp Asn Leu Val Lys Gly Ser Tyr Gly Phe Glu
    50                  55                  60

Ala Glu Phe Asn Lys Ser Gln Thr Ser Phe His Leu Lys Lys Pro Ser
65                  70                  75                  80

Ala Leu Val Ser Asp Ser Ala Leu Tyr Phe Cys Ala Val Arg Asp Gly
                85                  90                  95

Ala Asp Ser Trp Gly Lys Leu Gln Phe Gly Ala Gly Thr Gln Val Val
            100                 105                 110

Val Thr Pro
        115

<210> SEQ ID NO 14
<211> LENGTH: 115
<212> TYPE: PRT
<213> ORGANISM: Homo sapiens
<220> FEATURE:
<223> OTHER INFORMATION: beta variable chain for T cell receptor 7

<400> SEQUENCE: 14

```
Glu Thr Gly Val Thr Gln Thr Pro Arg His Leu Val Met Gly Met Thr
1               5                   10                  15

Asn Lys Lys Ser Leu Lys Cys Glu Gln His Leu Gly His Asn Ala Met
                20                  25                  30

Tyr Trp Tyr Lys Gln Ser Ala Lys Pro Leu Glu Leu Met Phe Val
            35                  40                  45

Tyr Ser Leu Glu Glu Arg Val Glu Asn Asn Ser Val Pro Ser Arg Phe
50                  55                  60

Ser Pro Glu Cys Pro Asn Ser Ser His Leu Phe Leu His Leu His Thr
65                  70                  75                  80

Leu Gln Pro Glu Asp Ser Ala Leu Tyr Leu Cys Ala Ser Ser Gln Arg
                85                  90                  95

Glu Gly Ile Ser Tyr Asn Glu Gln Phe Phe Gly Pro Gly Thr Arg Leu
                100                 105                 110

Thr Val Leu
        115
```

<210> SEQ ID NO 15
<211> LENGTH: 111
<212> TYPE: PRT
<213> ORGANISM: Homo sapiens
<220> FEATURE:
<223> OTHER INFORMATION: alpha variable chain for T cell receptor 8

<400> SEQUENCE: 15

```
Ala Gln Ser Val Ala Gln Pro Glu Asp Gln Val Asn Val Ala Glu Gly
1               5                   10                  15

Asn Pro Leu Thr Val Lys Cys Thr Tyr Ser Val Ser Gly Asn Pro Tyr
                20                  25                  30

Leu Phe Trp Tyr Val Gln Tyr Pro Asn Arg Gly Leu Gln Phe Leu Leu
            35                  40                  45

Lys Tyr Ile Thr Gly Asp Asn Leu Val Lys Gly Ser Tyr Gly Phe Glu
50                  55                  60

Ala Glu Phe Asn Lys Ser Gln Thr Ser Phe His Leu Lys Lys Pro Ser
65                  70                  75                  80

Ala Leu Val Ser Asp Ser Ala Leu Tyr Phe Cys Ala Gly Tyr Tyr Gly
                85                  90                  95

Gln Asn Phe Val Phe Gly Pro Gly Thr Arg Leu Ser Val Leu Pro
                100                 105                 110
```

<210> SEQ ID NO 16
<211> LENGTH: 112
<212> TYPE: PRT
<213> ORGANISM: Homo sapiens
<220> FEATURE:
<223> OTHER INFORMATION: beta variable chain for T cell receptor 8

<400> SEQUENCE: 16

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
                20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
50                  55                  60

Ser Val Ser Arg Glu Lys Lys Glu Arg Phe Ser Leu Ile Leu Glu Ser
65                  70                  75                  80
```

-continued

Ala Ser Thr Asn Gln Thr Ser Met Tyr Leu Cys Ala Ser Ser Phe Gln
                85                  90                  95

Gly Tyr Thr Glu Ala Phe Phe Gly Gln Gly Thr Arg Leu Thr Val Val
            100                 105                 110

<210> SEQ ID NO 17
<211> LENGTH: 113
<212> TYPE: PRT
<213> ORGANISM: Homo sapiens
<220> FEATURE:
<223> OTHER INFORMATION: alpha variable chain for T cell receptor 9

<400> SEQUENCE: 17

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Ser Gln Thr Gly Asp
                85                  90                  95

Ser Trp Gly Lys Phe Gln Phe Gly Ala Gly Thr Gln Val Val Val Thr
            100                 105                 110

Pro

<210> SEQ ID NO 18
<211> LENGTH: 116
<212> TYPE: PRT
<213> ORGANISM: Homo sapiens
<220> FEATURE:
<223> OTHER INFORMATION: beta variable chain for T cell receptor 9

<400> SEQUENCE: 18

Asp Thr Glu Val Thr Gln Thr Pro Lys His Leu Val Met Gly Met Thr
1               5                   10                  15

Asn Lys Lys Ser Leu Lys Cys Glu Gln His Met Gly His Arg Ala Met
            20                  25                  30

Tyr Trp Tyr Lys Gln Lys Ala Lys Lys Pro Pro Glu Leu Met Phe Val
        35                  40                  45

Tyr Ser Tyr Glu Lys Leu Ser Ile Asn Glu Ser Val Pro Ser Arg Phe
    50                  55                  60

Ser Pro Glu Cys Pro Asn Ser Ser Leu Leu Asn Leu His Leu His Ala
65                  70                  75                  80

Leu Gln Pro Glu Asp Ser Ala Leu Tyr Leu Cys Ala Ser Ser Gln Glu
                85                  90                  95

Phe Pro Gly Gln Gly Ser Tyr Glu Gln Tyr Phe Gly Pro Gly Thr Arg
            100                 105                 110

Leu Thr Val Thr
        115

<210> SEQ ID NO 19
<211> LENGTH: 112
<212> TYPE: PRT
<213> ORGANISM: Homo sapiens
<220> FEATURE:
<223> OTHER INFORMATION: alpha variable chain for T cell receptor 10

<400> SEQUENCE: 19

Ala Gln Ser Val Thr Gln Pro Asp Ile His Ile Thr Val Ser Glu Gly
1               5                   10                  15

Ala Ser Leu Glu Leu Arg Cys Asn Tyr Ser Tyr Gly Ala Thr Pro Tyr
                20                  25                  30

Leu Phe Trp Tyr Val Gln Ser Pro Gly Gln Gly Leu Gln Leu Leu Leu
            35                  40                  45

Lys Tyr Phe Ser Gly Asp Thr Leu Val Gln Gly Ile Lys Gly Phe Glu
        50                  55                  60

Ala Glu Phe Lys Arg Ser Gln Ser Ser Phe Asn Leu Arg Lys Pro Ser
65                  70                  75                  80

Val His Trp Ser Asp Ala Ala Glu Tyr Phe Cys Ala Ser Gly Asn Ala
                85                  90                  95

Gly Asn Met Leu Thr Phe Gly Gly Gly Thr Arg Leu Met Val Lys Pro
            100                 105                 110

<210> SEQ ID NO 20
<211> LENGTH: 116
<212> TYPE: PRT
<213> ORGANISM: Homo sapiens
<220> FEATURE:
<223> OTHER INFORMATION: beta variable chain for T cell receptor 10

<400> SEQUENCE: 20

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
                20                  25                  30

Ser Trp Tyr Arg Gln Asp Pro Gly Met Gly Leu Arg Leu Ile His Tyr
            35                  40                  45

Ser Val Gly Ala Gly Ile Thr Asp Gln Gly Glu Val Pro Asn Gly Tyr
        50                  55                  60

Asn Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Ser Pro Gly
                85                  90                  95

Thr Gly Ala Val Phe Phe Tyr Gly Tyr Thr Phe Gly Ser Gly Thr Arg
            100                 105                 110

Leu Thr Val Val
        115

<210> SEQ ID NO 21
<211> LENGTH: 113
<212> TYPE: PRT
<213> ORGANISM: Homo sapiens
<220> FEATURE:
<223> OTHER INFORMATION: alpha variable chain for T cell receptor 11

<400> SEQUENCE: 21

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
                20                  25                  30

Gln Trp Tyr Arg Gln Asn Ser Gly Arg Gly Leu Val His Leu Ile Leu
            35                  40                  45

```
Ile Arg Ser Asn Glu Arg Glu Lys His Ser Gly Arg Leu Arg Val Thr
 50                  55                  60

Leu Asp Thr Ser Lys Lys Ser Ser Leu Leu Ile Thr Ala Ser Arg
 65                  70                  75                  80

Ala Ala Asp Thr Ala Ser Tyr Phe Cys Ala Thr Asp Leu Asn Thr Gly
                     85                  90                  95

Thr Ala Ser Lys Leu Thr Phe Gly Thr Gly Thr Arg Leu Gln Val Thr
                100                 105                 110

Leu

<210> SEQ ID NO 22
<211> LENGTH: 113
<212> TYPE: PRT
<213> ORGANISM: Homo sapiens
<220> FEATURE:
<223> OTHER INFORMATION: beta variable chain for T cell receptor 11

<400> SEQUENCE: 22

Asp Thr Gly Val Ser Gln Asn Pro Arg His Lys Ile Thr Lys Arg Gly
 1               5                  10                  15

Gln Asn Val Thr Phe Arg Cys Asp Pro Ile Ser Glu His Asn Arg Leu
                 20                  25                  30

Tyr Trp Tyr Arg Gln Thr Leu Gly Gln Gly Pro Glu Phe Leu Thr Tyr
             35                  40                  45

Phe Gln Asn Glu Ala Gln Leu Glu Lys Ser Arg Leu Leu Ser Asp Arg
 50                  55                  60

Phe Ser Ala Glu Arg Pro Lys Gly Ser Phe Ser Thr Leu Glu Ile Gln
 65                  70                  75                  80

Arg Thr Glu Gln Gly Asp Ser Ala Met Tyr Leu Cys Ala Ser Ser Phe
                 85                  90                  95

Gln Gly Tyr Thr Glu Ala Phe Phe Gly Gln Gly Thr Arg Leu Thr Val
                100                 105                 110

Val

<210> SEQ ID NO 23
<211> LENGTH: 112
<212> TYPE: PRT
<213> ORGANISM: Homo sapiens
<220> FEATURE:
<223> OTHER INFORMATION: alpha variable chain for T cell receptor 12

<400> SEQUENCE: 23

Arg Lys Glu Val Glu Gln Asp Pro Gly Pro Phe Asn Val Pro Glu Gly
 1               5                  10                  15

Ala Thr Val Ala Phe Asn Cys Thr Tyr Ser Asn Ser Ala Ser Gln Ser
                 20                  25                  30

Phe Phe Trp Tyr Arg Gln Asp Cys Arg Lys Glu Pro Lys Leu Leu Met
             35                  40                  45

Ser Val Tyr Ser Ser Gly Asn Glu Asp Gly Arg Phe Thr Ala Gln Leu
 50                  55                  60

Asn Arg Ala Ser Gln Tyr Ile Ser Leu Leu Ile Arg Asp Ser Lys Leu
 65                  70                  75                  80

Ser Asp Ser Ala Thr Tyr Leu Cys Val Val Asn Ile Arg Gly Gly Ser
                 85                  90                  95

Gln Gly Asn Leu Ile Phe Gly Lys Gly Thr Lys Leu Ser Val Lys Pro
                100                 105                 110
```

```
<210> SEQ ID NO 24
<211> LENGTH: 111
<212> TYPE: PRT
<213> ORGANISM: Homo sapiens
<220> FEATURE:
<223> OTHER INFORMATION: beta variable chain for T cell receptor 12

<400> SEQUENCE: 24
```

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Gln Ile Val Asn Asp Phe Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser Ser Ala
                85                  90                  95

Asn Tyr Gly Tyr Thr Phe Gly Ser Gly Thr Arg Leu Thr Val Val
            100                 105                 110

```
<210> SEQ ID NO 25
<211> LENGTH: 107
<212> TYPE: PRT
<213> ORGANISM: Homo sapiens
<220> FEATURE:
<223> OTHER INFORMATION: alpha variable chain for T cell receptor 13

<400> SEQUENCE: 25
```

Gly Ile Gln Val Glu Gln Ser Pro Pro Asp Leu Ile Leu Gln Glu Gly
1               5                   10                  15

Ala Asn Ser Thr Leu Arg Cys Asn Phe Ser Asp Ser Val Asn Asn Leu
            20                  25                  30

Gln Trp Phe His Gln Asn Pro Trp Gly Gln Leu Ile Asn Leu Phe Tyr
        35                  40                  45

Ile Pro Ser Gly Thr Glu Gln Asn Gly Arg Leu Ser Ala Thr Thr Val
    50                  55                  60

Ala Thr Glu Arg Tyr Ser Leu Leu Tyr Ile Ser Ser Ser His Thr Thr
65                  70                  75                  80

Asp Ser Gly Val Tyr Phe Cys Ala Thr Gly Thr Ala Ser Lys Leu Thr
                85                  90                  95

Phe Gly Thr Gly Thr Arg Leu Gln Val Thr Leu
            100                 105

```
<210> SEQ ID NO 26
<211> LENGTH: 112
<212> TYPE: PRT
<213> ORGANISM: Homo sapiens
<220> FEATURE:
<223> OTHER INFORMATION: beta variable chain for T cell receptor 13

<400> SEQUENCE: 26
```

Gly Ala Gly Val Ser Gln Ser Pro Ser Asn Lys Val Thr Glu Lys Gly
1               5                   10                  15

Lys Asp Val Glu Leu Arg Cys Asp Pro Ile Ser Gly His Thr Ala Leu
            20                  25                  30

Tyr Trp Tyr Arg Gln Ser Leu Gly Gln Gly Leu Glu Phe Leu Ile Tyr
        35                  40                  45

Phe Gln Gly Asn Ser Ala Pro Asp Lys Ser Gly Leu Pro Ser Asp Arg
            50                  55                  60

Phe Ser Ala Glu Arg Thr Gly Gly Pro Val Ser Thr Leu Thr Ile Gln
 65                  70                  75                  80

Arg Thr Gln Gln Glu Asp Ser Ala Val Tyr Leu Cys Ala Ser Ser Ser
                    85                  90                  95

Ala Asn Tyr Gly Tyr Thr Phe Gly Ser Gly Thr Arg Leu Thr Val Val
                100                 105                 110

<210> SEQ ID NO 27
<211> LENGTH: 112
<212> TYPE: PRT
<213> ORGANISM: Homo sapiens
<220> FEATURE:
<223> OTHER INFORMATION: alpha variable chain for T cell receptor 14

<400> SEQUENCE: 27

Asp Ala Lys Thr Thr Gln Pro Thr Ser Met Asp Cys Ala Glu Gly Arg
 1               5                  10                  15

Ala Ala Asn Leu Pro Cys Asn His Ser Thr Ile Ser Gly Asn Glu Tyr
                20                  25                  30

Val Tyr Trp Tyr Arg Gln Ile His Ser Gln Gly Pro Gln Tyr Ile Ile
                35                  40                  45

His Gly Leu Lys Asn Asn Glu Thr Asn Glu Met Ala Ser Leu Ile Ile
            50                  55                  60

Thr Glu Asp Arg Lys Ser Ser Thr Leu Ile Leu Pro His Ala Thr Leu
 65                  70                  75                  80

Arg Asp Thr Ala Val Tyr Tyr Cys Ile Val Ser His Arg Val Gly Ser
                    85                  90                  95

Asn Tyr Gln Leu Ile Trp Gly Ala Gly Thr Lys Leu Ile Ile Lys Pro
                100                 105                 110

<210> SEQ ID NO 28
<211> LENGTH: 110
<212> TYPE: PRT
<213> ORGANISM: Homo sapiens
<220> FEATURE:
<223> OTHER INFORMATION: beta variable chain for T cell receptor 14

<400> SEQUENCE: 28

Glu Thr Gly Val Thr Gln Ser Pro Thr His Leu Ile Lys Thr Arg Gly
 1               5                  10                  15

Gln Gln Val Thr Leu Arg Cys Ser Ser Gln Ser Gly His Asn Thr Val
                20                  25                  30

Ser Trp Tyr Gln Gln Ala Leu Gly Gln Gly Pro Gln Phe Ile Phe Gln
                35                  40                  45

Tyr Tyr Arg Glu Glu Glu Asn Gly Arg Gly Asn Phe Pro Pro Arg Phe
            50                  55                  60

Ser Gly Leu Gln Phe Pro Asn Tyr Ser Ser Glu Leu Asn Val Asn Ala
 65                  70                  75                  80

Leu Glu Leu Asp Asp Ser Ala Leu Tyr Leu Cys Ala Ser Ser Ser Val
                    85                  90                  95

Asn Glu Gln Phe Phe Gly Pro Gly Thr Arg Leu Thr Val Leu
                100                 105                 110

<210> SEQ ID NO 29
<211> LENGTH: 107
<212> TYPE: PRT

<213> ORGANISM: Homo sapiens
<220> FEATURE:
<223> OTHER INFORMATION: alpha variable chain for T cell receptor 15

<400> SEQUENCE: 29

Arg Lys Glu Val Glu Gln Asp Pro Gly Pro Phe Asn Val Pro Glu Gly
1               5                   10                  15

Ala Thr Val Ala Phe Asn Cys Thr Tyr Ser Asn Ser Ala Ser Gln Ser
                20                  25                  30

Phe Phe Trp Tyr Arg Gln Asp Cys Arg Lys Glu Pro Lys Leu Leu Met
            35                  40                  45

Ser Ile Tyr Ser Ser Gly Asn Glu Asp Gly Arg Phe Thr Ala Gln Leu
        50                  55                  60

Asn Arg Ala Ser Gln Tyr Ile Ser Leu Leu Ile Arg Asp Ser Lys Leu
65                  70                  75                  80

Ser Asp Ser Ala Thr Tyr Leu Cys Val Val Arg Thr Asp Lys Leu Ile
                85                  90                  95

Phe Gly Thr Gly Thr Arg Leu Gln Val Phe Pro
            100                 105

<210> SEQ ID NO 30
<211> LENGTH: 115
<212> TYPE: PRT
<213> ORGANISM: Homo sapiens
<220> FEATURE:
<223> OTHER INFORMATION: beta variable chain for T cell receptor 15

<400> SEQUENCE: 30

Lys Ala Gly Val Thr Gln Thr Pro Arg Tyr Leu Ile Lys Thr Arg Gly
1               5                   10                  15

Gln Gln Val Thr Leu Ser Cys Ser Pro Ile Ser Gly His Arg Ser Val
                20                  25                  30

Ser Trp Tyr Gln Gln Thr Pro Gly Gln Gly Leu Gln Phe Leu Phe Glu
            35                  40                  45

Tyr Phe Ser Glu Thr Gln Arg Asn Lys Gly Asn Phe Pro Gly Arg Phe
        50                  55                  60

Ser Gly Arg Gln Phe Ser Asn Ser Arg Ser Glu Met Asn Val Ser Thr
65                  70                  75                  80

Leu Glu Leu Gly Asp Ser Ala Leu Tyr Leu Cys Ala Ser Ser Leu Asp
                85                  90                  95

Ser Gln Ser Ser Gly Asn Thr Ile Tyr Phe Gly Glu Gly Ser Trp Leu
            100                 105                 110

Thr Val Val
        115

<210> SEQ ID NO 31
<211> LENGTH: 110
<212> TYPE: PRT
<213> ORGANISM: Homo sapiens
<220> FEATURE:
<223> OTHER INFORMATION: alpha variable chain for T cell receptor 16

<400> SEQUENCE: 31

Gln Gln Pro Val Gln Ser Pro Gln Ala Val Ile Leu Arg Glu Gly Glu
1               5                   10                  15

Asp Ala Val Ile Asn Cys Ser Ser Ser Lys Ala Leu Tyr Ser Val His
                20                  25                  30

Trp Tyr Arg Gln Lys His Gly Glu Ala Pro Val Phe Leu Met Ile Leu
            35                  40                  45

Leu Lys Gly Gly Glu Gln Lys Gly His Glu Lys Ile Ser Ala Ser Phe
    50                  55                  60

Asn Glu Lys Arg Gln Gln Ser Ser Leu Tyr Leu Thr Ala Ser Gln Leu
65                  70                  75                  80

Ser Tyr Ser Gly Thr Tyr Phe Cys Gly Thr Glu Ile Pro Tyr Asp Tyr
                85                  90                  95

Lys Leu Ser Phe Gly Ala Gly Thr Thr Val Thr Val Arg Ala
                100                 105                 110

<210> SEQ ID NO 32
<211> LENGTH: 117
<212> TYPE: PRT
<213> ORGANISM: Homo sapiens
<220> FEATURE:
<223> OTHER INFORMATION: beta variable chain for T cell receptor 16

<400> SEQUENCE: 32

Gly Ala Val Val Ser Gln His Pro Ser Arg Val Ile Cys Lys Ser Gly
1               5                   10                  15

Thr Ser Val Lys Ile Glu Cys Arg Ser Leu Asp Phe Gln Ala Thr Thr
                20                  25                  30

Met Phe Trp Tyr Arg Gln Phe Pro Lys Gln Ser Leu Met Leu Met Ala
            35                  40                  45

Thr Ser Asn Glu Gly Ser Lys Ala Thr Tyr Glu Gln Gly Val Glu Lys
        50                  55                  60

Asp Lys Phe Leu Ile Asn His Ala Ser Leu Thr Leu Ser Thr Leu Thr
65                  70                  75                  80

Val Thr Ser Ala His Pro Glu Asp Ser Ser Phe Tyr Ile Cys Ser Ala
                85                  90                  95

Arg Gly Gly Arg Val Gly Thr Asp Met Gln Tyr Phe Gly Pro Gly Thr
                100                 105                 110

Arg Leu Thr Val Leu
        115

<210> SEQ ID NO 33
<211> LENGTH: 111
<212> TYPE: PRT
<213> ORGANISM: Homo sapiens
<220> FEATURE:
<223> OTHER INFORMATION: alpha variable chain for T cell receptor 17

<400> SEQUENCE: 33

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Lys Glu Asn Asn
                85                  90                  95

Ala Arg Leu Met Phe Gly Asp Gly Thr Gln Leu Val Val Lys Pro
                100                 105                 110

<210> SEQ ID NO 34
<211> LENGTH: 115
<212> TYPE: PRT
<213> ORGANISM: Homo sapiens
<220> FEATURE:
<223> OTHER INFORMATION: beta variable chain for T cell receptor 17

<400> SEQUENCE: 34

Gly Ala Val Val Ser Gln His Pro Ser Arg Val Ile Cys Lys Ser Gly
1               5                   10                  15

Thr Ser Val Lys Ile Glu Cys Arg Ser Leu Asp Phe Gln Asp Thr Thr
            20                  25                  30

Met Phe Trp Tyr Arg Gln Phe Pro Lys Gln Ser Leu Met Leu Met Ala
        35                  40                  45

Thr Ser Asn Glu Gly Ser Lys Ala Thr Tyr Glu Gln Gly Val Glu Lys
    50                  55                  60

Asp Lys Phe Leu Ile Asn His Ala Ser Leu Thr Leu Ser Thr Leu Thr
65                  70                  75                  80

Val Thr Ser Ala His Pro Glu Asp Ser Ser Phe Tyr Ile Cys Ser Ala
                85                  90                  95

Pro Arg Thr Leu Gly Asn Glu Gln Phe Phe Gly Pro Gly Thr Arg Leu
            100                 105                 110

Thr Val Leu
        115

<210> SEQ ID NO 35
<211> LENGTH: 117
<212> TYPE: PRT
<213> ORGANISM: Homo sapiens
<220> FEATURE:
<223> OTHER INFORMATION: alpha variable chain for T cell receptor 18

<400> SEQUENCE: 35

Ala Gln Ser Val Thr Gln Leu Asp Ser His Val Ser Val Ser Glu Gly
1               5                   10                  15

Thr Pro Val Leu Leu Arg Cys Asn Tyr Ser Ser Ser Tyr Ser Pro Ser
            20                  25                  30

Leu Phe Trp Tyr Val Gln His Pro Asn Lys Gly Leu Gln Leu Leu Leu
        35                  40                  45

Lys Tyr Thr Ser Ala Ala Thr Leu Val Lys Gly Ile Asn Gly Phe Glu
    50                  55                  60

Ala Glu Phe Lys Lys Ser Glu Thr Ser Phe His Leu Thr Lys Pro Ser
65                  70                  75                  80

Ala His Met Ser Asp Ala Ala Glu Tyr Phe Cys Val Val Ser Ala Arg
                85                  90                  95

Ser Leu Ser Gly Gly Tyr Asn Lys Leu Ile Phe Gly Ser Gly Thr Arg
            100                 105                 110

Leu Ser Ile Arg Pro
        115

<210> SEQ ID NO 36
<211> LENGTH: 115
<212> TYPE: PRT
<213> ORGANISM: Homo sapiens
<220> FEATURE:
<223> OTHER INFORMATION: beta variable chain for T cell receptor 18

<400> SEQUENCE: 36

Asp Ser Gly Val Thr Gln Thr Pro Lys His Leu Ile Thr Ala Thr Gly
1               5                   10                  15

Gln Arg Val Thr Leu Arg Cys Ser Pro Arg Ser Gly Asp Leu Ser Val
            20                  25                  30

Tyr Trp Tyr Gln Gln Ser Leu Asp Gln Gly Leu Gln Phe Leu Ile Gln
        35                  40                  45

Tyr Tyr Asn Gly Glu Glu Arg Ala Lys Gly Asn Ile Leu Glu Arg Phe
    50                  55                  60

Ser Ala Gln Gln Phe Pro Asp Leu His Ser Glu Leu Asn Leu Ser Ser
65                  70                  75                  80

Leu Glu Leu Gly Asp Ser Ala Leu Tyr Phe Cys Ala Ser Ser Thr Gly
                85                  90                  95

Gln Leu Ser Asn Thr Gly Glu Leu Phe Phe Gly Glu Gly Ser Arg Leu
            100                 105                 110

Thr Val Leu
        115

<210> SEQ ID NO 37
<211> LENGTH: 110
<212> TYPE: PRT
<213> ORGANISM: Homo sapiens
<220> FEATURE:
<223> OTHER INFORMATION: alpha variable chain for T cell receptor 19

<400> SEQUENCE: 37

Gln Gln Pro Val Gln Ser Pro Gln Ala Val Ile Leu Arg Glu Gly Glu
1               5                   10                  15

Asp Ala Val Ile Asn Cys Ser Ser Ser Lys Ala Leu Tyr Ser Val His
            20                  25                  30

Trp Tyr Arg Gln Lys His Gly Glu Ala Pro Val Phe Leu Met Ile Leu
        35                  40                  45

Leu Lys Gly Gly Glu Gln Lys Gly His Glu Lys Ile Ser Ala Ser Phe
    50                  55                  60

Asn Glu Lys Lys Gln Gln Ser Ser Leu Tyr Leu Thr Ala Ser Gln Leu
65                  70                  75                  80

Ser Tyr Ser Gly Thr Tyr Phe Cys Gly Thr Glu Ile Glu Asn Asp Tyr
                85                  90                  95

Lys Leu Ser Phe Gly Ala Gly Thr Thr Val Thr Val Arg Ala
            100                 105                 110

<210> SEQ ID NO 38
<211> LENGTH: 115
<212> TYPE: PRT
<213> ORGANISM: Homo sapiens
<220> FEATURE:
<223> OTHER INFORMATION: beta variable chain for T cell receptor 19

<400> SEQUENCE: 38

Asp Ser Gly Val Thr Gln Thr Pro Lys His Leu Ile Thr Ala Thr Gly
1               5                   10                  15

Gln Arg Val Thr Leu Arg Cys Ser Pro Arg Ser Gly Asp Leu Ser Val
            20                  25                  30

Tyr Trp Tyr Gln Gln Ser Leu Asp Gln Gly Leu Gln Phe Leu Ile Gln
        35                  40                  45

Tyr Tyr Asn Gly Glu Glu Arg Ala Lys Gly Asn Ile Leu Glu Arg Phe
    50                  55                  60

Ser Ala Gln Gln Phe Pro Asp Leu His Ser Glu Leu Asn Leu Ser Ser
65                  70                  75                  80

Leu Glu Leu Gly Asp Ser Ala Leu Tyr Phe Cys Ala Ser Ser Thr Gly

```
                    85                  90                  95
Gln Leu Ser Asn Thr Gly Glu Leu Phe Phe Gly Glu Gly Ser Arg Leu
                100                 105                 110

Thr Val Leu
        115

<210> SEQ ID NO 39
<211> LENGTH: 112
<212> TYPE: PRT
<213> ORGANISM: Homo sapiens
<220> FEATURE:
<223> OTHER INFORMATION: alpha variable chain for T cell receptor 20

<400> SEQUENCE: 39

Gly Gln Ser Leu Glu Gln Pro Ser Glu Val Thr Ala Val Glu Gly Ala
1               5                   10                  15

Ile Val Gln Ile Asn Cys Thr Tyr Gln Thr Ser Gly Phe Tyr Gly Leu
                20                  25                  30

Ser Trp Tyr Gln Gln His Asp Gly Gly Ala Pro Thr Phe Leu Ser Tyr
            35                  40                  45

Asn Ala Leu Asp Gly Leu Glu Glu Thr Gly Arg Phe Ser Ser Phe Leu
        50                  55                  60

Ser Arg Ser Asp Ser Tyr Gly Tyr Leu Leu Leu Gln Glu Leu Gln Met
65                  70                  75                  80

Lys Asp Ser Ala Ser Tyr Phe Cys Ala Val Arg Asp Arg Ser Gln Ala
                85                  90                  95

Gly Thr Ala Leu Ile Phe Gly Lys Gly Thr Thr Leu Ser Val Ser Ser
                100                 105                 110

<210> SEQ ID NO 40
<211> LENGTH: 112
<212> TYPE: PRT
<213> ORGANISM: Homo sapiens
<220> FEATURE:
<223> OTHER INFORMATION: beta variable chain for T cell receptor 20

<400> SEQUENCE: 40

Asp Ala Gly Val Thr Gln Ser Pro Thr His Leu Ile Lys Thr Arg Gly
1               5                   10                  15

Gln His Val Thr Leu Arg Cys Ser Pro Ile Ser Gly His Lys Ser Val
                20                  25                  30

Ser Trp Tyr Gln Gln Val Leu Gly Gln Gly Pro Gln Phe Ile Phe Gln
            35                  40                  45

Tyr Tyr Glu Lys Glu Glu Arg Gly Arg Gly Asn Phe Pro Asp Arg Phe
        50                  55                  60

Ser Ala Arg Arg Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Phe Asp
                85                  90                  95

Gly Thr Gly Glu Leu Phe Phe Gly Glu Gly Ser Arg Leu Thr Val Leu
                100                 105                 110

<210> SEQ ID NO 41
<211> LENGTH: 110
<212> TYPE: PRT
<213> ORGANISM: Homo sapiens
<220> FEATURE:
<223> OTHER INFORMATION: alpha variable chain for T cell receptor 21

<400> SEQUENCE: 41
```

-continued

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Phe Ser Gly Ser
                85                  90                  95

Arg Leu Thr Phe Gly Glu Gly Thr Gln Leu Thr Val Asn Pro
            100                 105                 110

<210> SEQ ID NO 42
<211> LENGTH: 112
<212> TYPE: PRT
<213> ORGANISM: Homo sapiens
<220> FEATURE:
<223> OTHER INFORMATION: beta variable chain for T cell receptor 21

<400> SEQUENCE: 42

Asn Ala Gly Val Thr Gln Thr Pro Lys Phe Arg Ile Leu Lys Ile Gly
1               5                   10                  15

Gln Ser Met Thr Leu Gln Cys Thr Gln Asp Met Asn His Asn Tyr Met
                20                  25                  30

Tyr Trp Tyr Arg Gln Asp Pro Gly Met Gly Leu Lys Leu Ile Tyr Tyr
            35                  40                  45

Ser Val Gly Ala Gly Ile Thr Asp Lys Gly Glu Val Pro Asn Gly Tyr
50                  55                  60

Asn Val Ser Arg Ser Thr Thr Glu Asp Phe Pro Leu Arg Leu Glu Leu
65                  70                  75                  80

Ala Ala Pro Ser Gln Thr Ser Val Tyr Phe Cys Ala Ser Arg Leu Trp
                85                  90                  95

Gly Asp Tyr Gly Tyr Thr Phe Gly Ser Gly Thr Arg Leu Thr Val Val
            100                 105                 110

<210> SEQ ID NO 43
<211> LENGTH: 112
<212> TYPE: PRT
<213> ORGANISM: Homo sapiens
<220> FEATURE:
<223> OTHER INFORMATION: alpha variable chain for T cell receptor 22

<400> SEQUENCE: 43

Ala Gln Ser Val Thr Gln Pro Asp Ile His Ile Thr Val Ser Glu Gly
1               5                   10                  15

Ala Ser Leu Glu Leu Arg Cys Asn Tyr Ser Tyr Gly Ala Thr Pro Tyr
                20                  25                  30

Leu Phe Trp Tyr Val Gln Ser Pro Gly Gln Gly Leu Gln Leu Leu Leu
            35                  40                  45

Lys Tyr Phe Ser Gly Asp Thr Leu Val Gln Gly Ile Lys Gly Phe Glu
50                  55                  60

Ala Glu Phe Lys Arg Ser Gln Ser Ser Phe Asn Leu Arg Lys Pro Ser
65                  70                  75                  80

Val His Trp Ser Asp Ala Ala Glu Tyr Phe Cys Ala Val Gly Gly Ala

```
                85                  90                  95
Gly Asn Met Leu Thr Phe Gly Gly Thr Arg Leu Met Val Lys Pro
            100                 105                 110

<210> SEQ ID NO 44
<211> LENGTH: 114
<212> TYPE: PRT
<213> ORGANISM: Homo sapiens
<220> FEATURE:
<223> OTHER INFORMATION: beta variable chain for T cell receptor 22

<400> SEQUENCE: 44

Gly Ala Val Val Ser Gln His Pro Ser Arg Val Ile Cys Lys Ser Gly
1               5                   10                  15

Thr Ser Val Lys Ile Glu Cys Arg Ser Leu Asp Phe Gln Ala Thr Thr
            20                  25                  30

Met Phe Trp Tyr Arg Gln Phe Pro Lys Gln Ser Leu Met Leu Met Ala
        35                  40                  45

Thr Ser Asn Glu Gly Ser Arg Ala Thr Tyr Glu Gln Gly Val Glu Lys
    50                  55                  60

Asp Lys Phe Leu Ile Asn His Ala Ser Leu Thr Leu Ser Thr Leu Thr
65                  70                  75                  80

Val Thr Ser Ala His Pro Glu Asp Ser Ser Phe Tyr Ile Cys Ser Ala
                85                  90                  95

Arg Asp Asn Ser Arg Glu Gln Tyr Phe Gly Pro Gly Thr Arg Leu Thr
            100                 105                 110

Val Thr

<210> SEQ ID NO 45
<211> LENGTH: 108
<212> TYPE: PRT
<213> ORGANISM: Homo sapiens
<220> FEATURE:
<223> OTHER INFORMATION: alpha variable chain for T cell receptor 23

<400> SEQUENCE: 45

Gly Glu Asp Val Glu Gln Ser Leu Phe Leu Ser Val Arg Glu Gly Asp
1               5                   10                  15

Ser Ser Val Ile Asn Cys Thr Tyr Thr Asp Ser Ser Ser Thr Tyr Leu
            20                  25                  30

Tyr Trp Tyr Lys Gln Glu Pro Gly Ala Gly Leu Gln Leu Leu Thr Tyr
        35                  40                  45

Ile Phe Ser Asn Met Asp Met Lys Gln Asp Gln Arg Leu Thr Val Leu
    50                  55                  60

Leu Asn Lys Lys Asp Lys His Leu Ser Leu Arg Ile Ala Asp Thr Gln
65                  70                  75                  80

Thr Gly Asp Ser Ala Ile Tyr Phe Cys Ala Val Ser Thr Gly Lys Leu
                85                  90                  95

Ile Phe Gly Gln Gly Thr Thr Leu Gln Val Lys Pro
            100                 105

<210> SEQ ID NO 46
<211> LENGTH: 115
<212> TYPE: PRT
<213> ORGANISM: Homo sapiens
<220> FEATURE:
<223> OTHER INFORMATION: beta variable chain for T cell receptor 23

<400> SEQUENCE: 46
```

```
Ser Ala Val Ile Ser Gln Lys Pro Ser Arg Asp Ile Cys Gln Arg Gly
1               5                   10                  15

Thr Ser Leu Thr Ile Gln Cys Gln Val Asp Ser Gln Val Thr Met Met
            20                  25                  30

Phe Trp Tyr Arg Gln Gln Pro Gly Gln Ser Leu Thr Leu Ile Ala Thr
            35                  40                  45

Ala Asn Gln Gly Ser Glu Ala Thr Tyr Glu Ser Gly Phe Val Ile Asp
            50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser Val Gly
            85                  90                  95

Thr Gly Gly Thr Asn Glu Lys Leu Phe Phe Gly Ser Gly Thr Gln Leu
            100                 105                 110

Ser Val Leu
        115
```

<210> SEQ ID NO 47
<211> LENGTH: 110
<212> TYPE: PRT
<213> ORGANISM: Homo sapiens
<220> FEATURE:
<223> OTHER INFORMATION: alpha variable chain for T cell receptor 24

<400> SEQUENCE: 47

```
Arg Lys Glu Val Glu Gln Asp Pro Gly Pro Phe Asn Val Pro Glu Gly
1               5                   10                  15

Ala Thr Val Ala Phe Asn Cys Thr Tyr Ser Asn Ser Ala Ser Gln Ser
            20                  25                  30

Phe Phe Trp Tyr Arg Gln Asp Cys Arg Lys Glu Pro Lys Leu Leu Met
            35                  40                  45

Ser Val Tyr Ser Ser Gly Asn Glu Asp Gly Arg Phe Thr Ala Gln Leu
            50                  55                  60

Asn Arg Ala Ser Gln Tyr Ile Ser Leu Leu Ile Arg Asp Ser Lys Leu
65                  70                  75                  80

Ser Asp Ser Ala Thr Tyr Leu Cys Val Val Asn Val Ala Asn Asp Tyr
            85                  90                  95

Lys Leu Ser Phe Gly Ala Gly Thr Thr Val Thr Val Arg Ala
            100                 105                 110
```

<210> SEQ ID NO 48
<211> LENGTH: 115
<212> TYPE: PRT
<213> ORGANISM: Homo sapiens
<220> FEATURE:
<223> OTHER INFORMATION: beta variable chain for T cell receptor 24

<400> SEQUENCE: 48

```
Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
            35                  40                  45

Ser Gln Ile Val Asn Asp Phe Gln Lys Gly Asp Ile Ala Glu Gly Tyr
            50                  55                  60

Ser Val Ser Arg Glu Lys Lys Glu Ser Phe Pro Leu Thr Val Thr Ser
65                  70                  75                  80
```

```
Ala Gln Lys Asn Pro Thr Ala Phe Tyr Leu Cys Ala Ser Ser Ile Ala
                85                  90                  95

His Val Ala Gly Gly Asn Glu Gln Phe Phe Gly Pro Gly Thr Arg Leu
            100                 105                 110

Thr Val Leu
        115

<210> SEQ ID NO 49
<211> LENGTH: 111
<212> TYPE: PRT
<213> ORGANISM: Homo sapiens
<220> FEATURE:
<223> OTHER INFORMATION: alpha variable chain for T cell receptor 25

<400> SEQUENCE: 49

Gln Lys Glu Val Glu Gln Asp Pro Gly Pro Leu Ser Val Pro Glu Gly
1               5                   10                  15

Ala Ile Val Ser Leu Asn Cys Thr Tyr Ser Asn Ser Ala Phe Gln Tyr
            20                  25                  30

Phe Met Trp Tyr Arg Gln Tyr Ser Arg Lys Gly Pro Glu Leu Leu Met
        35                  40                  45

Tyr Thr Tyr Ser Ser Gly Asn Lys Glu Asp Gly Arg Phe Thr Ala Gln
    50                  55                  60

Val Asp Lys Ser Ser Lys Tyr Ile Ser Leu Phe Ile Arg Asp Ser Gln
65                  70                  75                  80

Pro Ser Asp Ser Ala Thr Tyr Leu Cys Ala Met Thr Ser Thr Gly Ala
                85                  90                  95

Asp Lys Leu Ile Phe Gly Thr Gly Thr Arg Leu Gln Val Phe Pro
            100                 105                 110

<210> SEQ ID NO 50
<211> LENGTH: 110
<212> TYPE: PRT
<213> ORGANISM: Homo sapiens
<220> FEATURE:
<223> OTHER INFORMATION: beta variable chain for T cell receptor 25

<400> SEQUENCE: 50

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Gly Gly Val Ser
                85                  90                  95

Tyr Glu Gln Tyr Phe Gly Pro Gly Thr Arg Leu Thr Val Thr
            100                 105                 110

<210> SEQ ID NO 51
<211> LENGTH: 111
<212> TYPE: PRT
<213> ORGANISM: Homo sapiens
<220> FEATURE:
<223> OTHER INFORMATION: alpha variable chain for T cell receptor 26
```

<400> SEQUENCE: 51

Gly Glu Asn Val Glu Gln His Pro Ser Thr Leu Ser Val Gln Glu Gly
1               5                   10                  15

Asp Ser Ala Val Ile Lys Cys Thr Tyr Ser Asp Ser Ala Ser Asn Tyr
            20                  25                  30

Phe Pro Trp Tyr Lys Gln Glu Leu Gly Lys Arg Pro Gln Leu Ile Ile
        35                  40                  45

Asp Ile Arg Ser Asn Val Gly Glu Lys Lys Asp Gln Arg Val Ala Val
    50                  55                  60

Thr Leu Ser Lys Thr Ala Lys His Phe Ser Leu His Ile Thr Glu Thr
65                  70                  75                  80

Gln Pro Glu Asp Ser Ala Val Tyr Phe Cys Ala Ala Ser Lys Gly Gly
                85                  90                  95

Thr Pro Leu Val Phe Gly Lys Gly Thr Arg Leu Ser Val Ile Ala
            100                 105                 110

<210> SEQ ID NO 52
<211> LENGTH: 114
<212> TYPE: PRT
<213> ORGANISM: Homo sapiens
<220> FEATURE:
<223> OTHER INFORMATION: beta variable chain for T cell receptor 26

<400> SEQUENCE: 52

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Ser Ser
                85                  90                  95

Pro Gly Gln Thr Asn Gly Tyr Thr Phe Gly Ser Gly Thr Arg Leu Thr
            100                 105                 110

Val Val

<210> SEQ ID NO 53
<211> LENGTH: 111
<212> TYPE: PRT
<213> ORGANISM: Homo sapiens
<220> FEATURE:
<223> OTHER INFORMATION: alpha variable chain for T cell receptor 27

<400> SEQUENCE: 53

Ala Gln Ser Val Thr Gln Leu Asp Ser Gln Val Pro Val Phe Glu Glu
1               5                   10                  15

Ala Pro Val Glu Leu Arg Cys Asn Tyr Ser Ser Ser Val Ser Val Tyr
            20                  25                  30

Leu Phe Trp Tyr Val Gln Tyr Pro Asn Gln Gly Leu Gln Leu Leu Leu
        35                  40                  45

Lys Tyr Leu Ser Gly Ser Thr Leu Val Glu Ser Ile Asn Gly Phe Glu
    50                  55                  60

```
Ala Glu Phe Asn Lys Ser Gln Thr Ser Phe His Leu Arg Lys Pro Ser
 65                  70                  75                  80

Val His Ile Ser Asp Thr Ala Glu Tyr Phe Arg Gly Asn Ser Gly Asn
                 85                  90                  95

Thr Pro Leu Val Phe Gly Lys Gly Thr Arg Leu Ser Val Ile Ala
            100                 105                 110

<210> SEQ ID NO 54
<211> LENGTH: 114
<212> TYPE: PRT
<213> ORGANISM: Homo sapiens
<220> FEATURE:
<223> OTHER INFORMATION: beta variable chain for T cell receptor 27

<400> SEQUENCE: 54

Asp Thr Ala Val Ser Gln Thr Pro Lys Tyr Leu Val Thr Gln Met Gly
 1               5                  10                  15

Asn Asp Lys Ser Val Lys Cys Glu Gln Asn Leu Gly His Asp Thr Met
                20                  25                  30

Tyr Trp Tyr Lys Gln Asp Ser Lys Lys Phe Leu Lys Ile Met Phe Ser
             35                  40                  45

Tyr Asn Asn Lys Glu Leu Ile Ile Asn Glu Thr Val Pro Asn Arg Phe
 50                  55                  60

Ser Pro Lys Ser Pro Asp Lys Ala His Leu Asn Leu His Ile Asn Ser
 65                  70                  75                  80

Leu Glu Leu Gly Asp Ser Ala Val Tyr Phe Cys Ala Ser Ser Gln Asp
                 85                  90                  95

Gln Thr Gly Gly His Glu Gln Phe Phe Gly Pro Gly Thr Arg Leu Thr
            100                 105                 110

Val Leu

<210> SEQ ID NO 55
<211> LENGTH: 110
<212> TYPE: PRT
<213> ORGANISM: Homo sapiens
<220> FEATURE:
<223> OTHER INFORMATION: alpha variable chain for T cell receptor 28

<400> SEQUENCE: 55

Thr Gln Leu Leu Glu Gln Ser Pro Gln Phe Leu Ser Ile Gln Glu Gly
 1               5                  10                  15

Glu Asn Leu Thr Val Tyr Cys Asn Ser Ser Ser Val Phe Ser Ser Leu
                20                  25                  30

Gln Trp Tyr Arg Gln Glu Pro Gly Glu Gly Pro Val Leu Leu Val Thr
             35                  40                  45

Val Val Thr Gly Gly Glu Val Lys Lys Leu Lys Arg Leu Thr Phe Gln
 50                  55                  60

Phe Gly Asp Ala Arg Lys Asp Ser Ser Leu His Ile Thr Ala Ala Gln
 65                  70                  75                  80

Pro Gly Asp Thr Gly Leu Tyr Leu Cys Ala Gly Ala Val Gly Asn Ala
                 85                  90                  95

Arg Leu Met Phe Gly Asp Gly Thr Gln Leu Val Val Lys Pro
            100                 105                 110

<210> SEQ ID NO 56
<211> LENGTH: 110
<212> TYPE: PRT
<213> ORGANISM: Homo sapiens
<220> FEATURE:
```

<223> OTHER INFORMATION: beta variable chain for T cell receptor 28

<400> SEQUENCE: 56

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ile Glu Gly Gly
            85                  90                  95

Thr Glu Ala Phe Phe Gly Gln Gly Thr Arg Leu Thr Val Val
            100                 105                 110

<210> SEQ ID NO 57
<211> LENGTH: 111
<212> TYPE: PRT
<213> ORGANISM: Homo sapiens
<220> FEATURE:
<223> OTHER INFORMATION: alpha variable chain for T cell receptor 29

<400> SEQUENCE: 57

Gly Gln Gln Val Met Gln Ile Pro Gln Tyr Gln His Val Gln Glu Gly
1               5                   10                  15

Glu Asp Phe Thr Thr Tyr Cys Asn Ser Ser Thr Thr Leu Ser Asn Ile
            20                  25                  30

Gln Trp Tyr Lys Gln Arg Pro Gly Gly His Pro Val Phe Leu Ile Gln
        35                  40                  45

Leu Val Lys Ser Gly Glu Val Lys Lys Gln Lys Arg Leu Thr Phe Gln
    50                  55                  60

Phe Gly Glu Ala Lys Lys Asn Ser Ser Leu His Ile Thr Ala Thr Gln
65                  70                  75                  80

Thr Thr Asp Val Gly Thr Tyr Phe Cys Ala Gly Ala Gly Ala Gly Ser
            85                  90                  95

Tyr Gln Leu Thr Phe Gly Lys Gly Thr Lys Leu Ser Val Ile Pro
            100                 105                 110

<210> SEQ ID NO 58
<211> LENGTH: 115
<212> TYPE: PRT
<213> ORGANISM: Homo sapiens
<220> FEATURE:
<223> OTHER INFORMATION: beta variable chain for T cell receptor 29

<400> SEQUENCE: 58

Lys Ala Gly Val Thr Gln Thr Pro Arg Tyr Leu Ile Lys Thr Arg Gly
1               5                   10                  15

Gln Gln Val Thr Leu Ser Cys Ser Pro Ile Ser Gly His Arg Ser Val
            20                  25                  30

Ser Trp Tyr Gln Gln Thr Pro Gly Gln Gly Leu Gln Phe Leu Phe Glu
        35                  40                  45

Tyr Phe Ser Glu Thr Gln Arg Asn Lys Gly Asn Phe Pro Gly Arg Phe
    50                  55                  60

Ser Gly Arg Gln Phe Ser Asn Ser Arg Ser Glu Met Asn Val Ser Thr

```
                 65                  70                  75                  80
Leu Glu Leu Gly Asp Ser Ala Leu Tyr Leu Cys Ala Ser Ser Leu Glu
                 85                  90                  95

Gly Gln Ala Ser Ser Tyr Glu Gln Tyr Phe Gly Pro Gly Thr Arg Leu
            100                 105                 110

Thr Val Thr
        115

<210> SEQ ID NO 59
<211> LENGTH: 111
<212> TYPE: PRT
<213> ORGANISM: Homo sapiens
<220> FEATURE:
<223> OTHER INFORMATION: alpha variable chain for T cell receptor 30

<400> SEQUENCE: 59

Gln Lys Glu Val Glu Gln Asp Pro Gly Pro Leu Ser Val Pro Glu Gly
1               5                  10                  15

Ala Ile Val Ser Leu Asn Cys Thr Tyr Ser Asn Ser Ala Phe Gln Tyr
            20                  25                  30

Phe Met Trp Tyr Arg Gln Tyr Ser Arg Lys Gly Pro Glu Leu Leu Met
        35                  40                  45

Tyr Thr Tyr Ser Ser Gly Asn Lys Glu Asp Gly Arg Phe Thr Ala Gln
    50                  55                  60

Val Asp Lys Ser Ser Lys Tyr Ile Ser Leu Phe Ile Arg Asp Ser Gln
65                  70                  75                  80

Pro Ser Asp Ser Ala Thr Tyr Leu Cys Ala Met Arg Ala Gly Gly Ser
                85                  90                  95

Tyr Ile Pro Thr Phe Gly Arg Gly Thr Ser Leu Ile Val His Pro
            100                 105                 110

<210> SEQ ID NO 60
<211> LENGTH: 115
<212> TYPE: PRT
<213> ORGANISM: Homo sapiens
<220> FEATURE:
<223> OTHER INFORMATION: beta variable chain for T cell receptor 30

<400> SEQUENCE: 60

Glu Ala Gln Val Thr Gln Asn Pro Arg Tyr Leu Ile Thr Val Thr Gly
1               5                  10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Asp Trp Thr
                85                  90                  95

Ala Arg Arg Gly Ile Ser Pro Leu His Phe Gly Asn Gly Thr Arg Leu
            100                 105                 110

Thr Val Thr
        115

<210> SEQ ID NO 61
<211> LENGTH: 111
```

```
<212> TYPE: PRT
<213> ORGANISM: Homo sapiens
<220> FEATURE:
<223> OTHER INFORMATION: alpha variable chain for T cell receptor 31

<400> SEQUENCE: 61

Gly Gln Gln Val Met Gln Ile Pro Gln Tyr Gln His Val Gln Glu Gly
1               5                   10                  15

Glu Asp Phe Thr Thr Tyr Cys Asn Ser Ser Thr Thr Leu Ser Asn Ile
            20                  25                  30

Gln Trp Tyr Lys Gln Arg Pro Gly His Pro Val Phe Leu Ile Gln
        35                  40                  45

Leu Val Lys Ser Gly Glu Val Lys Lys Gln Lys Arg Leu Thr Phe Gln
    50                  55                  60

Phe Gly Glu Ala Lys Lys Asn Ser Ser Leu His Ile Thr Ala Thr Gln
65                  70                  75                  80

Thr Thr Asp Val Gly Thr Tyr Phe Cys Ala Gly Asp Gly Thr Ser Tyr
                85                  90                  95

Asp Lys Val Ile Phe Gly Pro Gly Thr Ser Leu Ser Val Ile Pro
            100                 105                 110

<210> SEQ ID NO 62
<211> LENGTH: 114
<212> TYPE: PRT
<213> ORGANISM: Homo sapiens
<220> FEATURE:
<223> OTHER INFORMATION: beta variable chain for T cell receptor 31

<400> SEQUENCE: 62

Ser Ala Val Ile Ser Gln Lys Pro Ser Arg Asp Ile Cys Gln Arg Gly
1               5                   10                  15

Thr Ser Leu Thr Ile Gln Cys Gln Val Asp Ser Gln Val Thr Met Met
            20                  25                  30

Phe Trp Tyr Arg Gln Gln Pro Gly Gln Ser Leu Thr Leu Ile Ala Thr
        35                  40                  45

Ala Asn Gln Gly Ser Glu Ala Thr Tyr Glu Ser Gly Phe Val Ile Asp
    50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser Val Leu
                85                  90                  95

Ala Gly Asn Ser Tyr Glu Gln Tyr Phe Gly Pro Gly Thr Arg Leu Thr
            100                 105                 110

Val Thr

<210> SEQ ID NO 63
<211> LENGTH: 109
<212> TYPE: PRT
<213> ORGANISM: Homo sapiens
<220> FEATURE:
<223> OTHER INFORMATION: alpha variable chain for T cell receptor 32

<400> SEQUENCE: 63

Gly Gln Ser Leu Glu Gln Pro Ser Glu Val Thr Ala Val Glu Gly Ala
1               5                   10                  15

Ile Val Gln Ile Asn Cys Thr Tyr Gln Thr Ser Gly Phe Tyr Gly Leu
            20                  25                  30

Ser Trp Tyr Gln Gln His Asp Gly Gly Ala Pro Thr Phe Leu Ser Tyr
        35                  40                  45
```

```
Asn Ala Leu Asp Gly Leu Glu Glu Thr Gly Arg Phe Ser Ser Phe Leu
            50                  55                  60

Ser Arg Ser Asp Ser Tyr Gly Tyr Leu Leu Leu Gln Glu Leu Gln Met
 65                  70                  75                  80

Lys Asp Ser Ala Ser Tyr Phe Cys Ala Val Arg Asp Asn Asp Tyr Lys
                85                  90                  95

Leu Ser Phe Gly Ala Gly Thr Thr Val Thr Val Arg Ala
            100                 105
```

<210> SEQ ID NO 64
<211> LENGTH: 114
<212> TYPE: PRT
<213> ORGANISM: Homo sapiens
<220> FEATURE:
<223> OTHER INFORMATION: beta variable chain for T cell receptor 32

<400> SEQUENCE: 64

```
Lys Ala Gly Val Thr Gln Thr Pro Arg Tyr Leu Ile Lys Thr Arg Gly
 1                   5                  10                  15

Gln Gln Val Thr Leu Ser Cys Ser Pro Ile Ser Gly His Arg Ser Val
                20                  25                  30

Ser Trp Tyr Gln Gln Thr Pro Gly Gln Gly Leu Gln Phe Leu Phe Glu
            35                  40                  45

Tyr Phe Ser Glu Thr Gln Arg Asn Lys Gly Asn Phe Pro Gly Arg Phe
    50                  55                  60

Ser Gly Arg Gln Phe Ser Asn Ser Arg Ser Glu Met Asn Val Ser Thr
 65                  70                  75                  80

Leu Glu Leu Gly Asp Ser Ala Leu Tyr Leu Cys Ala Ser Ser Leu Ala
                85                  90                  95

Glu Gln Gly Met Tyr Glu Gln Tyr Phe Gly Pro Gly Thr Arg Leu Thr
            100                 105                 110

Val Thr
```

<210> SEQ ID NO 65
<211> LENGTH: 110
<212> TYPE: PRT
<213> ORGANISM: Homo sapiens
<220> FEATURE:
<223> OTHER INFORMATION: alpha variable chain for T cell receptor 33

<400> SEQUENCE: 65

```
Glu Asp Gln Val Thr Gln Ser Pro Glu Ala Leu Arg Leu Gln Glu Gly
 1                   5                  10                  15

Glu Ser Ser Ser Leu Asn Cys Ser Tyr Thr Val Ser Gly Leu Arg Gly
                20                  25                  30

Leu Phe Trp Tyr Arg Gln Asp Pro Gly Lys Gly Pro Glu Phe Leu Phe
            35                  40                  45

Thr Leu Tyr Ser Ala Gly Glu Glu Lys Glu Lys Glu Arg Leu Lys Ala
    50                  55                  60

Thr Leu Thr Lys Lys Glu Ser Phe Leu His Ile Thr Ala Pro Lys Pro
 65                  70                  75                  80

Glu Asp Ser Ala Thr Tyr Leu Cys Ala Val Leu Gly Gly Ala Thr Asn
                85                  90                  95

Lys Leu Ile Phe Gly Thr Gly Thr Leu Leu Ala Val Gln Pro
            100                 105                 110
```

<210> SEQ ID NO 66

<211> LENGTH: 113
<212> TYPE: PRT
<213> ORGANISM: Homo sapiens
<220> FEATURE:
<223> OTHER INFORMATION: beta variable chain for T cell receptor 33

<400> SEQUENCE: 66

Glu Ala Asp Ile Tyr Gln Thr Pro Arg Tyr Leu Val Ile Gly Thr Gly
1               5                   10                  15

Lys Lys Ile Thr Leu Glu Cys Ser Gln Thr Met Gly His Asp Lys Met
            20                  25                  30

Tyr Trp Tyr Gln Gln Asp Pro Gly Met Glu Leu His Leu Ile His Tyr
        35                  40                  45

Ser Tyr Gly Val Asn Ser Thr Glu Lys Gly Asp Leu Ser Ser Glu Ser
    50                  55                  60

Thr Val Ser Arg Ile Arg Thr Glu His Phe Pro Leu Thr Leu Glu Ser
65                  70                  75                  80

Ala Arg Pro Ser His Thr Ser Gln Tyr Leu Cys Ala Ser Ser Gly Gly
                85                  90                  95

Ala Thr Gly Gly Glu Gln Tyr Phe Gly Pro Gly Thr Arg Leu Thr Val
            100                 105                 110

Thr

<210> SEQ ID NO 67
<211> LENGTH: 112
<212> TYPE: PRT
<213> ORGANISM: Homo sapiens
<220> FEATURE:
<223> OTHER INFORMATION: alpha variable chain for T cell receptor 34

<400> SEQUENCE: 67

Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Ser Val Phe Ser Ser Leu
            20                  25                  30

Gln Trp Tyr Arg Gln Glu Pro Gly Glu Gly Pro Val Leu Leu Val Thr
        35                  40                  45

Val Val Thr Gly Gly Glu Val Lys Lys Leu Lys Arg Leu Thr Phe Gln
    50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Gly Thr Leu Asn Ser Gly
                85                  90                  95

Asn Thr Pro Leu Val Phe Gly Lys Gly Thr Arg Leu Ser Val Ile Ala
            100                 105                 110

<210> SEQ ID NO 68
<211> LENGTH: 114
<212> TYPE: PRT
<213> ORGANISM: Homo sapiens
<220> FEATURE:
<223> OTHER INFORMATION: beta variable chain for T cell receptor 34

<400> SEQUENCE: 68

Ser Ala Val Ile Ser Gln Lys Pro Ser Arg Asp Ile Cys Gln Arg Gly
1               5                   10                  15

Thr Ser Leu Thr Ile Gln Cys Gln Val Asp Ser Gln Val Thr Met Met
            20                  25                  30

Phe Trp Tyr Arg Gln Gln Pro Gly Gln Ser Leu Thr Leu Ile Ala Thr

```
                35                  40                  45
Ala Asn Gln Gly Ser Glu Ala Thr Tyr Glu Ser Gly Phe Val Ile Asp
        50                  55                  60
Lys Phe Pro Ile Ser Arg Pro Asn Leu Thr Phe Ser Thr Leu Thr Val
 65                  70                  75                  80
Ser Asn Met Ser Pro Glu Asp Ser Ser Ile Tyr Leu Cys Ser Val Gly
                85                  90                  95
Thr Gly Gly Tyr Gln Tyr Phe Gly Pro Gly Thr Arg Leu Thr
            100                 105                 110
Val Thr

<210> SEQ ID NO 69
<211> LENGTH: 115
<212> TYPE: PRT
<213> ORGANISM: Homo sapiens
<220> FEATURE:
<223> OTHER INFORMATION: alpha variable chain for T cell receptor 35

<400> SEQUENCE: 69

Ala Gln Thr Val Thr Gln Ser Gln Pro Glu Met Ser Val Gln Glu Ala
 1               5                  10                  15
Glu Thr Val Thr Leu Ser Cys Thr Tyr Asp Thr Ser Glu Asn Asn Tyr
                20                  25                  30
Tyr Leu Phe Trp Tyr Lys Gln Pro Ser Arg Gln Met Ile Leu Val
            35                  40                  45
Ile Arg Gln Glu Ala Tyr Lys Gln Gln Asn Ala Thr Glu Asn Arg Phe
        50                  55                  60
Ser Val Asn Phe Gln Lys Ala Ala Lys Ser Phe Ser Leu Lys Ile Ser
 65                  70                  75                  80
Asp Ser Gln Leu Gly Asp Thr Ala Met Tyr Phe Cys Ala Phe Met Gly
                85                  90                  95
Val Asp Ser Asn Tyr Gln Leu Ile Trp Gly Ala Gly Thr Lys Leu Ile
            100                 105                 110
Ile Lys Pro
       115

<210> SEQ ID NO 70
<211> LENGTH: 114
<212> TYPE: PRT
<213> ORGANISM: Homo sapiens
<220> FEATURE:
<223> OTHER INFORMATION: beta variable chain for T cell receptor 35

<400> SEQUENCE: 70

Ser Ala Val Ile Ser Gln Lys Pro Ser Arg Asp Ile Cys Gln Arg Gly
 1               5                  10                  15
Thr Ser Leu Thr Ile Gln Cys Gln Val Asp Ser Gln Val Thr Met Met
                20                  25                  30
Phe Trp Tyr Arg Gln Gln Pro Gly Gln Ser Leu Thr Leu Ile Ala Thr
            35                  40                  45
Ala Asn Gln Gly Ser Glu Ala Thr Tyr Glu Ser Gly Phe Val Ile Asp
        50                  55                  60
Lys Phe Pro Ile Ser Arg Pro Asn Leu Thr Phe Ser Thr Leu Thr Val
 65                  70                  75                  80
Ser Asn Met Ser Pro Glu Asp Ser Ser Ile Tyr Leu Cys Ser Val Val
                85                  90                  95
Pro Ala Asn Ser Tyr Glu Gln Tyr Phe Gly Pro Gly Thr Arg Leu Thr
```

Val Thr

<210> SEQ ID NO 71
<211> LENGTH: 109
<212> TYPE: PRT
<213> ORGANISM: Homo sapiens
<220> FEATURE:
<223> OTHER INFORMATION: alpha variable chain for T cell receptor 36

<400> SEQUENCE: 71

Arg Lys Glu Val Glu Gln Asp Pro Gly Pro Phe Asn Val Pro Glu Gly
1               5                   10                  15

Ala Thr Val Ala Phe Asn Cys Thr Tyr Ser Asn Ser Ala Ser Gln Ser
            20                  25                  30

Phe Phe Trp Tyr Arg Gln Asp Cys Arg Lys Glu Pro Lys Leu Leu Met
        35                  40                  45

Ser Val Tyr Ser Ser Gly Asn Glu Asp Gly Arg Phe Thr Ala Gln Leu
    50                  55                  60

Asn Arg Ala Ser Gln Tyr Ile Ser Leu Leu Ile Arg Asp Ser Lys Leu
65                  70                  75                  80

Ser Asp Ser Ala Thr Tyr Leu Cys Val Val Asn Lys Asp Asn Ala Arg
                85                  90                  95

Leu Met Phe Gly Asp Gly Thr Gln Leu Val Val Lys Pro
            100                 105

<210> SEQ ID NO 72
<211> LENGTH: 113
<212> TYPE: PRT
<213> ORGANISM: Homo sapiens
<220> FEATURE:
<223> OTHER INFORMATION: beta variable chain for T cell receptor 36

<400> SEQUENCE: 72

Ser Ala Val Ile Ser Gln Lys Pro Ser Arg Asp Ile Cys Gln Arg Gly
1               5                   10                  15

Thr Ser Leu Thr Ile Gln Cys Gln Val Asp Ser Gln Val Thr Met Met
            20                  25                  30

Phe Trp Tyr Arg Gln Gln Pro Gly Gln Ser Leu Thr Leu Ile Ala Thr
        35                  40                  45

Ala Asn Gln Gly Ser Glu Ala Thr Tyr Glu Ser Gly Phe Val Ile Asp
    50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser His Trp
                85                  90                  95

Glu Pro Asn Thr Glu Ala Phe Phe Gly Gln Gly Thr Arg Leu Thr Val
            100                 105                 110

Val

<210> SEQ ID NO 73
<211> LENGTH: 109
<212> TYPE: PRT
<213> ORGANISM: Homo sapiens
<220> FEATURE:
<223> OTHER INFORMATION: alpha variable chain for T cell receptor 37

<400> SEQUENCE: 73

Gly Gln Gln Leu Asn Gln Ser Pro Gln Ser Met Phe Ile Gln Glu Gly

```
                1               5                  10                 15
            Glu Asp Val Ser Met Asn Cys Thr Ser Ser Ser Ile Phe Asn Thr Trp
                               20                 25                 30

Leu Trp Tyr Lys Gln Asp Pro Gly Glu Cys Pro Val Leu Leu Ile Ala
                           35                 40                 45

Leu Tyr Lys Ala Gly Glu Leu Thr Ser Asn Gly Arg Leu Thr Ala Gln
                       50                 55                 60

Phe Gly Ile Thr Arg Lys Asp Ser Phe Leu Asn Ile Ser Ala Ser Ile
            65                 70                 75                 80

Pro Ser Asp Val Gly Ile Tyr Phe Cys Ala Gly Gln Thr Gly Asn Lys
                               85                 90                 95

Leu Val Phe Gly Ala Gly Thr Ile Leu Arg Val Lys Ser
                           100                105

<210> SEQ ID NO 74
<211> LENGTH: 112
<212> TYPE: PRT
<213> ORGANISM: Homo sapiens
<220> FEATURE:
<223> OTHER INFORMATION: beta variable chain for T cell receptor 37

<400> SEQUENCE: 74

Ser Gln Thr Ile His Gln Trp Pro Ala Thr Leu Val Gln Pro Val Gly
            1               5                  10                 15

Ser Pro Leu Ser Leu Glu Cys Thr Val Glu Gly Thr Ser Asn Pro Asn
                               20                 25                 30

Leu Tyr Trp Tyr Arg Gln Ala Ala Gly Arg Gly Leu Gln Leu Leu Phe
                           35                 40                 45

Tyr Ser Val Gly Ile Gly Gln Ile Ser Ser Glu Val Pro Gln Asn Leu
                       50                 55                 60

Ser Ala Ser Arg Pro Gln Asp Arg Gln Phe Ile Leu Ser Ser Lys Lys
            65                 70                 75                 80

Leu Leu Leu Ser Asp Ser Gly Phe Tyr Leu Cys Ala Trp Ser Thr Glu
                               85                 90                 95

Arg Val Glu Gly Tyr Thr Phe Gly Ser Gly Thr Arg Leu Thr Val Val
                           100                105                110

<210> SEQ ID NO 75
<211> LENGTH: 113
<212> TYPE: PRT
<213> ORGANISM: Homo sapiens
<220> FEATURE:
<223> OTHER INFORMATION: alpha variable chain for T cell receptor 38

<400> SEQUENCE: 75

Gln Lys Glu Val Glu Gln Asp Pro Gly Pro Leu Ser Val Pro Glu Gly
            1               5                  10                 15

Ala Ile Val Ser Leu Asn Cys Thr Tyr Ser Asn Ser Ala Phe Gln Tyr
                               20                 25                 30

Phe Met Trp Tyr Arg Gln Tyr Ser Arg Lys Gly Pro Glu Leu Leu Met
                           35                 40                 45

Tyr Thr Tyr Ser Ser Gly Asn Lys Glu Asp Gly Arg Phe Thr Ala Gln
                       50                 55                 60

Val Asp Lys Ser Ser Lys Tyr Ile Ser Leu Phe Ile Arg Asp Ser Gln
            65                 70                 75                 80

Pro Ser Asp Ser Ala Thr Tyr Leu Cys Ala Met Ser Leu Ser Gly Gly
                               85                 90                 95
```

```
Gly Ala Asp Gly Leu Thr Phe Gly Lys Gly Thr His Leu Ile Ile Gln
                100                 105                 110

Pro

<210> SEQ ID NO 76
<211> LENGTH: 113
<212> TYPE: PRT
<213> ORGANISM: Homo sapiens
<220> FEATURE:
<223> OTHER INFORMATION: beta variable chain for T cell receptor 38

<400> SEQUENCE: 76

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Asp
                85                  90                  95

Arg Leu Tyr Asn Glu Gln Phe Phe Gly Pro Gly Thr Arg Leu Thr Val
            100                 105                 110

Leu

<210> SEQ ID NO 77
<211> LENGTH: 111
<212> TYPE: PRT
<213> ORGANISM: Homo sapiens
<220> FEATURE:
<223> OTHER INFORMATION: alpha variable chain for T cell receptor 39

<400> SEQUENCE: 77

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Tyr Ser Gly Asn
                85                  90                  95

Thr Pro Leu Val Phe Gly Lys Gly Thr Arg Leu Ser Val Ile Ala
            100                 105                 110

<210> SEQ ID NO 78
<211> LENGTH: 114
<212> TYPE: PRT
<213> ORGANISM: Homo sapiens
<220> FEATURE:
<223> OTHER INFORMATION: beta variable chain for T cell receptor 39

<400> SEQUENCE: 78
```

```
Asp Thr Ala Val Ser Gln Thr Pro Lys Tyr Leu Val Thr Gln Met Gly
1               5                   10                  15

Asn Asp Lys Ser Ile Lys Cys Glu Gln Asn Leu Gly His Asp Thr Met
            20                  25                  30

Tyr Trp Tyr Lys Gln Asp Ser Lys Lys Phe Leu Lys Ile Met Phe Ser
        35                  40                  45

Tyr Asn Asn Lys Glu Leu Ile Ile Asn Glu Thr Val Pro Asn Arg Phe
    50                  55                  60

Ser Pro Lys Ser Pro Asp Lys Ala Leu Leu Asn Leu His Ile Asn Ser
65                  70                  75                  80

Leu Glu Leu Gly Asp Ser Ala Val Tyr Phe Cys Ala Ser Ser Ala Arg
                85                  90                  95

Pro Glu Phe Thr Asp Thr Gln Tyr Phe Gly Pro Gly Thr Arg Leu Thr
                100                 105                 110

Val Leu

<210> SEQ ID NO 79
<211> LENGTH: 112
<212> TYPE: PRT
<213> ORGANISM: Homo sapiens
<220> FEATURE:
<223> OTHER INFORMATION: alpha variable chain for T cell receptor 40

<400> SEQUENCE: 79

Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Ser Val Phe Ser Ser Leu
            20                  25                  30

Gln Trp Tyr Arg Gln Glu Pro Gly Glu Gly Pro Val Leu Leu Val Thr
        35                  40                  45

Val Val Thr Gly Gly Glu Val Lys Lys Leu Lys Arg Leu Thr Phe Gln
    50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Gly Ser Arg Trp Gly Gly
                85                  90                  95

Trp Gly Lys Leu Gln Phe Gly Ala Gly Thr Gln Val Val Val Thr Pro
                100                 105                 110

<210> SEQ ID NO 80
<211> LENGTH: 115
<212> TYPE: PRT
<213> ORGANISM: Homo sapiens
<220> FEATURE:
<223> OTHER INFORMATION: beta variable chain for T cell receptor 40

<400> SEQUENCE: 80

Asp Thr Gly Val Ser Gln Asn Pro Arg His Lys Ile Thr Lys Arg Gly
1               5                   10                  15

Gln Asn Val Thr Phe Arg Cys Asp Pro Ile Ser Glu His Asn Arg Leu
            20                  25                  30

Tyr Trp Tyr Arg Gln Thr Leu Gly Gln Gly Pro Glu Phe Leu Thr Tyr
        35                  40                  45

Phe Gln Asn Glu Ala Gln Leu Glu Lys Ser Arg Leu Leu Ser Asp Arg
    50                  55                  60

Phe Ser Ala Glu Arg Pro Lys Gly Ser Phe Ser Thr Leu Glu Ile Gln
65                  70                  75                  80
```

Arg Thr Glu Gln Gly Asp Ser Ala Met Tyr Leu Cys Ala Ser Ser Leu
                85                  90                  95

Trp Ala Val Asn Thr Gly Glu Leu Phe Phe Gly Glu Gly Ser Arg Leu
            100                 105                 110

Thr Val Leu
        115

<210> SEQ ID NO 81
<211> LENGTH: 113
<212> TYPE: PRT
<213> ORGANISM: Homo sapiens
<220> FEATURE:
<223> OTHER INFORMATION: alpha variable chain for T cell receptor 41

<400> SEQUENCE: 81

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Lys Val
                85                  90                  95

Gly Asn Glu Lys Leu Thr Phe Gly Thr Gly Thr Arg Leu Thr Ile Ile
            100                 105                 110

Pro

<210> SEQ ID NO 82
<211> LENGTH: 115
<212> TYPE: PRT
<213> ORGANISM: Homo sapiens
<220> FEATURE:
<223> OTHER INFORMATION: beta variable chain for T cell receptor 41

<400> SEQUENCE: 82

Gly Ala Val Val Ser Gln His Pro Ser Arg Val Ile Cys Lys Ser Gly
1               5                   10                  15

Thr Ser Val Lys Ile Glu Cys Arg Ser Leu Asp Phe Gln Ala Thr Thr
            20                  25                  30

Met Phe Trp Tyr Arg Gln Phe Pro Lys Gln Ser Leu Met Leu Met Ala
        35                  40                  45

Thr Ser Asn Glu Gly Ser Lys Ala Thr Tyr Glu Gln Gly Val Glu Lys
    50                  55                  60

Asp Lys Phe Leu Ile Asn His Ala Ser Leu Thr Leu Ser Thr Leu Thr
65                  70                  75                  80

Val Thr Ser Ala His Pro Glu Asp Ser Ser Phe Tyr Ile Cys Ser Ala
                85                  90                  95

Arg Val Ala Gly Arg Tyr Gly Tyr Thr Phe Gly Ser Gly Thr Arg Leu
            100                 105                 110

Thr Val Val
        115

<210> SEQ ID NO 83
<211> LENGTH: 106

```
<212> TYPE: PRT
<213> ORGANISM: Homo sapiens
<220> FEATURE:
<223> OTHER INFORMATION: alpha variable chain for T cell receptor 42

<400> SEQUENCE: 83

Lys Asp Gln Val Phe Gln Pro Ser Thr Val Ala Ser Ser Glu Gly Ala
1               5                   10                  15

Val Val Glu Ile Phe Cys Asn His Ser Val Ser Asn Ala Tyr Asn Phe
            20                  25                  30

Phe Trp Tyr Leu His Phe Pro Gly Cys Ala Pro Arg Leu Leu Val Lys
        35                  40                  45

Gly Ser Lys Pro Ser Gln Gln Gly Arg Tyr Asn Met Thr His Glu Arg
    50                  55                  60

Phe Ser Ser Ser Leu Leu Ile Leu Gln Val Arg Glu Ala Asp Ala Ala
65                  70                  75                  80

Val Tyr Tyr Cys Ala Val Glu Asp Pro Asn Asp Tyr Lys Leu Ser Phe
                85                  90                  95

Gly Ala Gly Thr Thr Val Thr Val Arg Ala
            100                 105

<210> SEQ ID NO 84
<211> LENGTH: 115
<212> TYPE: PRT
<213> ORGANISM: Homo sapiens
<220> FEATURE:
<223> OTHER INFORMATION: beta variable chain for T cell receptor 42

<400> SEQUENCE: 84

Gly Ala Gly Val Ser Gln Ser Pro Ser Asn Lys Val Thr Glu Lys Gly
1               5                   10                  15

Lys Asp Val Glu Leu Arg Cys Asp Pro Ile Ser Gly His Thr Ala Leu
            20                  25                  30

Tyr Trp Tyr Arg Gln Ser Leu Gly Gln Gly Leu Glu Phe Leu Ile Tyr
        35                  40                  45

Phe Gln Gly Asn Ser Ala Pro Asp Lys Ser Gly Leu Pro Ser Asp Arg
    50                  55                  60

Phe Ser Ala Glu Arg Thr Gly Gly Ser Val Ser Thr Leu Thr Ile Gln
65                  70                  75                  80

Arg Thr Gln Gln Glu Asp Ser Ala Val Tyr Ile Cys Ala Ser Ser Pro
                85                  90                  95

Asp Gly Thr Ser Gly Tyr Glu Gln Tyr Phe Gly Pro Gly Thr Arg Leu
            100                 105                 110

Thr Val Thr
        115
```